US011643478B2

(12) United States Patent
Jin et al.

(10) Patent No.: US 11,643,478 B2
(45) Date of Patent: May 9, 2023

(54) LOW-MOLECULAR-WEIGHT HOLOTHURIAN GLYCOSAMINOGLYCAN AND USE THEREOF

(71) Applicants: Suzhou Yi-hua Biomedical Technology co., Ltd, Jiangsu (CN); Suzhou Ronnsi Pharma Co., Ltd., Jiangsu (CN)

(72) Inventors: Yongsheng Jin, Jiangsu (CN); Xiujuan Ding, Jiangsu (CN); Wu Chen, Jiangsu (CN); Xiaoming Li, Jiangsu (CN); Junting Sun, Jiangsu (CN); Yihao Zhu, Jiangsu (CN); Xiaohua Lu, Jiangsu (CN); Caijuan Jin, Jiangsu (CN); Hua Zhou, Jiangsu (CN); Ningxia Wang, Jiangsu (CN); Yongbao Li, Jiangsu (CN); Qiaoyun Zhou, Jiangsu (CN); Jiangen Qian, Jiangsu (CN); Xi Chong, Jiangsu (CN); Yiming Yao, Jiangsu (CN); Yi Jiang, Jiangsu (CN)

( * ) Notice: Subject to any disclaimer, the term of this patent is extended or adjusted under 35 U.S.C. 154(b) by 0 days.

(21) Appl. No.: 17/775,588

(22) PCT Filed: Nov. 19, 2019

(86) PCT No.: PCT/CN2019/119414
§ 371 (c)(1),
(2) Date: May 10, 2022

(87) PCT Pub. No.: WO2021/092979
PCT Pub. Date: May 20, 2021

(65) Prior Publication Data

US 2022/0340690 A1 Oct. 27, 2022

(30) Foreign Application Priority Data

Nov. 12, 2019 (CN) ........................ 201911102517.0

(51) Int. Cl.
*C08B 37/00* (2006.01)
*A61P 25/28* (2006.01)
*A61P 29/00* (2006.01)
*A61P 35/04* (2006.01)
*A61P 9/14* (2006.01)
*A61K 31/726* (2006.01)

(52) U.S. Cl.
CPC ........ *C08B 37/0063* (2013.01); *A61K 31/726* (2013.01); *A61P 9/14* (2018.01); *A61P 25/28* (2018.01); *A61P 29/00* (2018.01); *A61P 35/04* (2018.01)

(58) Field of Classification Search
CPC ....... A61K 31/726; A61K 31/737; A61P 7/02; C08B 37/0063
USPC .......................................................... 536/53
See application file for complete search history.

(56) References Cited

U.S. PATENT DOCUMENTS

2019/0151350 A1 5/2019 Zhu et al.

FOREIGN PATENT DOCUMENTS

| | | | |
|---|---|---|---|
| CN | 104610459 | A | 5/2015 |
| CN | 106349397 | A | 1/2017 |
| CN | 106349407 | A | 1/2017 |
| JP | 09143202 | A | 6/1997 |
| JP | 2003252906 | A | 9/2003 |
| WO | WO2005058976 | A2 | 6/2005 |

OTHER PUBLICATIONS

Better Health Channel; Oct. 31, 2014.*

* cited by examiner

*Primary Examiner* — Layla D Berry
(74) *Attorney, Agent, or Firm* — OPES IP Consulting Co. Ltd

(57) ABSTRACT

Provided is a low-molecular-weight holothurian glycosarninoglycan, with the constituent units thereof being a glucuronic acid group, an N-acetaminogalactose group and a fucose group, and a sulfate ester group or acetyl ester group thereof. Glucuronic acid and N-acetaminogalactose are interconnected via β(1-3) and β(1-4) glucosidic bonds to form a backbone of a disaccharide repeating structural unit, and a fucose group is connected to the backbone as a side chain. On a molar ratio basis, the ratio of the glucuronic acid group:the N-acetaminogalactose group:the fucose group is 1:(0.8-1.2):(0.6-1.2). In the structure of the low-molecular-weight holothurian glycosaminoglycan, 10-30% of glucuronic acid groups are modified, on the 2-position, with a sulfate ester group, and the rest are hydroxyl groups; and a proportion of 10-30% of fucose groups is modified, on the 2-position, with an acetyl ester group, and the rest are hydroxyl or sulfate ester groups. The low-molecular-weight holothurian glycosarninoglycan of the present invention has anti-inflammation, anti-vasculopathy, anti-tumor or anti-tumor-metastasis functions, and the effect of improving learning and memory abilities, and can be used for preparing a related drug or health-care product.

12 Claims, 8 Drawing Sheets

LOW-MOLECULAR-WEIGHT HOLOTHURIAN GLYCOSAMINOGLYCAN AND USE THEREOF

FIELD

The present invention belongs to the field of biological medicine and health care product, in particular relates to a low-molecular-weight holothurian glycosaminoglycan and use for preparing drugs or health-care products thereof.

BACKGROUND

Holothurian glycosaminoglycan (HG) extracted from the molluscous holothurian is a special sulfate glycosaminoglycan with a fucose side-chain, the constitutional unit of the holothurian glycosaminoglycan includes glucuronic acid (GlcA, U), aminogalactose (GalN, A), and fucose (Fuc, F) and sulfate ester (—$OSO_3$—, S) thereof (Huizeng Fan et al., Acta Pharmaceutica Sinica, 1983, 18(3): 203; Ken-ichiro Y et al., Tetrahedron Letters, 1992, 33(34): 4959-4962).

According to the prior art, there is generality of natural HG. The constitutional unit of the holothurian glycosaminoglycan includes GlcA, GalN (N-acetylaminogalactose (GalNAc) is main) and Fuc, the GlcA and GalN are interactively connected through β (1-3) and β (1-4) glucosidic bond to form a backbone of a disaccharide repetitive structural unit [-GlcAβ (1-3)-GalNAcβ (1-4)-]. Fuc is connected to the backbone in a side chain form, and the backbone is similar with chondroitin sulfate E in mammals (Vieira R P et al., J. Biol. Chem., 1991, 266: 13530-13536).

There are differences in the composition ratio of monosaccharide and the structure between the natural HGs extracted from different kinds of holothurians. Except for the different composition ratio of monosaccharide, it has been reported that the main difference in the backbone of HG is the percent of the position 4 sulphating, the position 6 sulphating and the position 4,6 sulphating of GalNAc (GalNAc4S, GalNAc6S and GalNAc4S6S). The position 4 and 6 of GalNAc in the backbone of HG extracted from *S. japonicus* are all sulphated (Ken-ichiro Y et al., Tetrahedron Letters, 1992, 33(34):4959-4962). Only the position 4 of GalNAc in the backbone of HG extracted from *H. leucospilota* is sulphated, while the position 6 isn't sulphated (Huizeng Fan et al., Acta Pharmaceutica Sinica, 1980, 18(3): 203). The backbone of HG extracted from *L. grisea* has 53% GalNAc6S, 4% GalNAc4S and 12% GalNAc4S6S, and has 31% unsulphated GalNAc (Lubor Borsig et al. J. Biol. Chem. 2007, 282: 14984). On the other hand, the main difference in the side chain (Fuc) of HG is the sulphating position and composition ratio. For example, all of the HGs extracted from *S. japonicus* and *L. grisea* have three kinds of side chain Fuc, known as 2,4-disulfate ester Fuc (Fuc2S4S), 3,4-disulfate ester Fuc (Fuc3S4S) and 4-sulfate ester Fuc (Fuc4S), but the composition ratio of side chain Fuc of HGs extracted from *S. japonicus* and *L. grisea* is different (Ken-ichiro Y et al., Tetrahedron Letters, 1992, 33(34): 4959-4962; Paulo A S. et al., J. Biol. Chem., 1996, 271: 23973).

According to the reported literatures, the structure of natural HG can be summed up as the formula shown below:

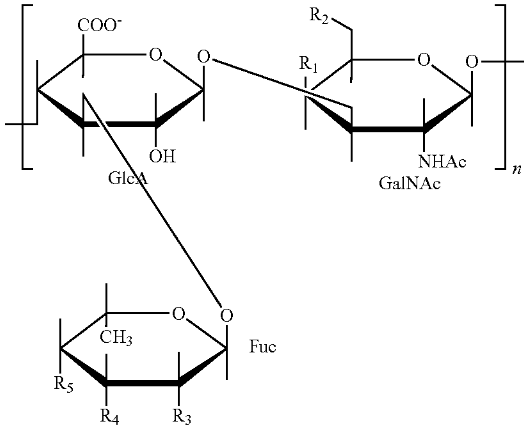

$R_1$—$R_5$ = —OH 或 —$OSO_3^-$

Available information shows that HG has many biological activities and functions. Natural HG being a highly sulfated glycosaminoglycan has significant anti-coagulant and anti-thrombotic activity (Huizeng Fan et al., Acta Pharmaceutica Sinica, 1980, 18(3): 203 et al.). Its anti-coagulant function does not depend on Antithrombin III (AT-III), which is different from heparin, and can act on multiple coagulation factor targets (Paulo A S. et al., J. Biol. Chem., 1996, 271: 23973). HG also has anti-inflammation, anti-tumor and lipid metabolism mediation functions (Lubor Borsig et al. J. Biol. Chem. 2007, 282: 14984; Tovar et al., Atherosclerosis, 1996, 126: 185-195).

Although HG has many biological activities, it is still difficult to apply to clinic, because HG has an activity of inducing platelet aggregation, this activity is similar with that of heparin. Data show that pharmacodynamic-dose HG extracted from *Japonicus* can decrease platelet count when it is injected to blood vessel in vivo (Li J Z et al., Thromb. Haemostas., 1998, 59(3): 435). The platelet count decreasing can induce immune thrombocytopenia which is similar with Heparin Induced Thrombocytopenia (HIT), and induce hemorrhage possibly, even induce serious or fatal disseminated intravascular coagulation. Reported is that decreasing the molecular weight of HG can reduce or avoid inducing platelet aggregation, this method improves the application security of HG.

In order to solve the difficulties in the application of HG and its derivatives, the applicant filed a chinese patent application named "depolymerized holothurian glycosaminoglycan composition and preparation method and application thereof" on Jul. 23, 2015 (CN201510438139.9), this patent disclosed a low-molecular-weight depolymerized holothurian glycosaminoglycan (dHG), which has low anti-coagulation activity, anti-tumor or anti-tumor-metastasis function and low toxic or side effect. But dHG has the problem of unsatisfactory pharmacological activity, which limits its application.

SUMMARY OF THE DISCLOSURE

To solve the above technical problems and provide HG derivative with better pharmacological activity and more suitable clinical application, a low-molecular-weight holothurian glycosaminoglycan (LHG) provided by the present invention, the LHG has two unique molecular structure characteristics: one is that 10-30% of glucuronic acid groups in backbone are modified, on the 2-position, with a sulfate ester group (GlcA2S); another is that 10-30% of fucose groups on side chain is modified, on the 2-position, with an acetyl ester group (Fuc2Ac). HG or HG derivatives with the two molecular structural characteristics have not been reported. In addition, LHG provided by the present invention has low anticoagulation activity and weak activity of inducing platelet aggregation, but it has anti-inflammation, anti-vasculopathy, anti-tumor or anti-tumor-metastasis functions, and the effect of improving learning and memory abilities. LHG provided by the present invention can be used for preparing a related drug or health-care product for prevention and treatment.

The present invention provides the following technical solutions:

An object of the present invention is to provide a low-molecular-weight holothurian glycosaminoglycan characterized by that the structure shown in the formula below:

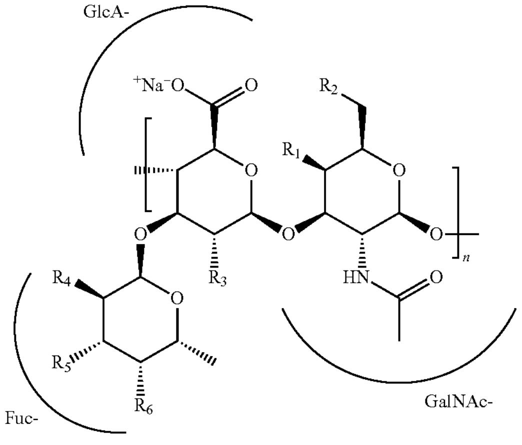

the constituent unit of said low-molecular-weight holothurian glycosaminoglycan include a glucuronic acid group (GlcA), an N-acetylaminogalactosyl group (GalNAc), and a fucose group (Fuc), and sodium sulfate ester, acetyl ester group or sodium thereof, the glucuronic acid group and the N-acetylaminogalactosyl group are interconnected via β(1-3) and β(1-4) glucosidic bonds to form a backbone of a disaccharide repeating structural unit, and the fucose group is connected to the backbone as a side chain, on a molar ratio basis, the ratio of the glucuronic acid group:the N-acetylaminogalactosyl group:the fucose group is 1:(0.8-1.2):(0.6-1.2), in the structure of the low-molecular-weight holothurian glycosaminoglycan, the n is between 1-32, the —$R_1$, —$R_2$, —$R_4$ and —$R_6$ are hydroxyl groups or sodium sulfate ester, 10-30% of the —$R_3$ of the glucuronic acid groups is modified by a sodium sulfate ester, and the rest are the hydroxyl groups, 10-30% of the —$R_5$ of the fucose groups is modified by an acetyl ester group, and the rest are the hydroxyl groups or sodium sulfate ester.

Said low-molecular-weight holothurian glycosaminoglycan is its sodium salt form, sodium is connected to carboxyl group or sulfate ester group with ionic bonds.

The second object of the present invention is to provide a low-molecular-weight holothurian glycosaminoglycan with a sylvite, calcium salt, lithium salt or zinc salt form, wherein the low-molecular-weight holothurian glycosaminoglycan has the similar structure with said low-molecular-weight holothurian glycosaminoglycan, but the sodium is replaced with corresponding potassium, calcium, lithium or zinc. The conversion of metal salt form can be implemented by the common methods in this art field, such as using cationic resin adsorption to remove sodium ion, and then adding specific metal salt to prepare low-molecular-weight holothurian glycosaminoglycan with other salt form, finally purified by alcohol precipitation or other methods. These low-molecular-weight holothurian glycosaminoglycans with metal salt forms can meet the needs of different ionic forms in specific application environments.

The third object of the present invention is to provide an application of the low-molecular-weight holothurian glycosaminoglycan for preparing the drugs or health-care products for prevention and treatment of inflammation, vasculopathy, tumors or tumor-related diseases and senile dementia.

According to the implementation of the above technical solutions, the present invention has the following advantages compared with the prior art:

LHG provided by the present invention can regulate platelet activity and has anti-inflammation, anti-vasculopathy, anti-tumor or anti-tumor-metastasis functions, and the effect of improving learning and memory abilities. Added acceptable carrier in drug or health-care product industry, LHG can be active material, used for preparing the drugs or health-care products for prevention and treatment of inflammation, vasculopathy, tumors, senile dementia and related diseases.

DETAILED DESCRIPTION

Figure 1A:
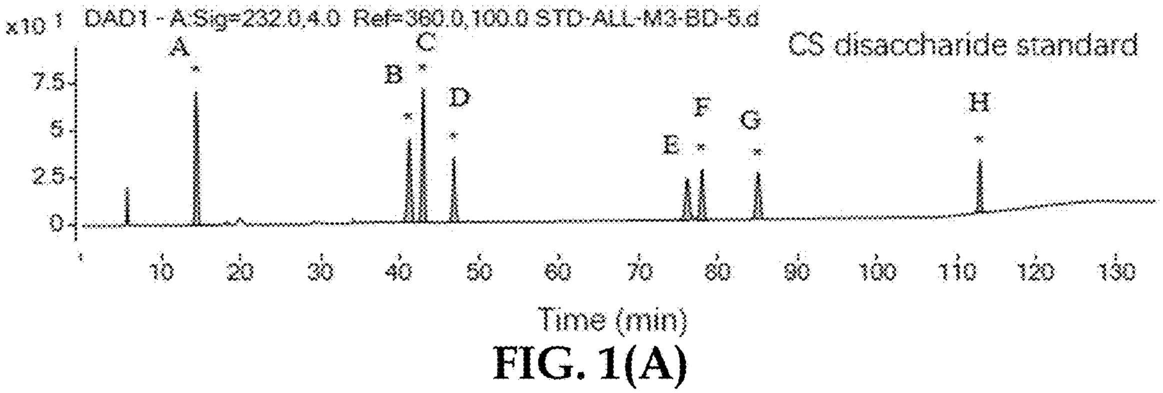
FIG. 1 is HPLC results of structural characteristics of disaccharide repeating structural unit in backbone of LHG provided by embodiment 3 of the present invention, wherein the results of the disaccharide standards are shown in FIG. 1 (A), the results of Sample 1-M, Sample 2-M, Sample 3-M, Sample 4-M, Sample 5-M and Sample 6-M are shown in FIG. 1 (B).

The present invention will be further described in detail below with reference to specific embodiments, but the present invention is not limited to the following embodiments. The implementation conditions applied in the embodiments can be further adjusted according to different requirements of specific use, and the implementation conditions not specified are the conventional conditions in the industry. All other embodiments obtained by a person of ordinary skill in the art without creative work fall within the protection scope of the present invention.

Embodiment 1: Preparation of Low-Molecular-Weight Holothurian Glycosaminoglycan LHG Provided by the present embodiment is Preparation of LHG, the preparation process includes the following steps:
Step 1: Extraction and Purification of Holothurian Glycosaminoglycan (HG)
20 L of water was added to 10 kg of dried market holothurian. After soaking overnight, the holothurian was minced. Holothurian homogenate was transferred to 100 L of reactor, additional 50 L of water, 0.8 Kg of sodium carbonate and 1.6 Kg of sodium chloride were added, then the reactor was heated to 50° C., lasted for a while. 0.2 Kg of alkaline proteinase 2709 was added to the mixture. The enzymolysis lasted 6 hours at 50° C. After the enzymolysis was end, the solution is filtered with gauze for removing gravel. The filtrate was transferred into resin reactor (LANXESS 55428) with 5 Kg wet weight, and was stirred and resin adsorbed for 3 hours. The resin was filtered and collected, washed with water for 3 times, then washed with 15 L of 4% NaCl (w/w) for 3 times. The resin was eluted for 3 times with 15 L of 15% NaCl (w/w), mixture solution of resin and NaCl was stirred 15~30 min at room temperature for every time, the eluents of 3 times were combined. The combined elution (45 L) was precipitated with 45 L of 95% ethanol at stirring. The precipitate was centrifuged and collected to obtain the HG. The obtained HG was dissolved in 2 L of 3% NaCl (w/w), precipitated with 3 L of 95% ethanol, then dehydrated with 95% ethanol, dried to obtain 125.2 g of HG pure product.
Step 2: Depolymerized Preparation of Low-Molecular-Weight Holothurian Glycosaminoglycan (LHG)
100 g of the HG pure product prepared in step 1 was completely dissolved in 0.9 L of water, then 10 mL of acetic acid glacial and 100 mL of 30% hydrogen peroxide were added. The reaction solution was heated to 50° C. and reacted for some time. During the reaction, sampling and samples were sent to HPLC to determinate the molecular weight distribution. When the time of reaction is about 24 h, sample of target object with weight-average molecular weight 7400 Da was detected, then reaction was terminated. NaOH concentrated solution is added into reaction solution to adjust pH to neutral, then 100 g of NaCl was added and completely dissolved by stirring. 2 L of 95% ethanol is added, the sediment is isolated by centrifugation to obtain the target LHG crude product. The LHG crude product is redissolved with 1 L of 3% NaCl, then the LHG was precipitated out by adding 1.5 L of 95% ethanol. Said redissolve and said precipitation were repeated once. Finally, sediment was dehydrated with 95% ethanol, vacuum dried to obtain 73.5 g of the LHG, the batch number is LHG-L180501.
Step 3: Preparation of Other Batch LHG
Provided by the present embodiment is preparation of other batch or other source LHG.
Specifically, preparation of other batch LHG has two steps according to said step 1 and said step 2, but quantity of material (or concentration) and general operating parameters (such as temperature, time and pH) are different, and the number of using general purification procedure (such as brine redissolve and alcohol precipitation) is also different. The preparation process of these batches LHG was monitored by HPLC to determinate the molecular weight distribution, weight-average molecular weight of target LHG is all below 10000 Da. Batch number, holothurian and yield of some typical batches of the present embodiment are presented in Table 1.

TABLE 1

| Items/Batch number | LHG-L180501 | LHG-181101 | LHG-181102 | LHG-181103 | LHG-190301 | LHG-190501 |
|---|---|---|---|---|---|---|
| holothurian | 10 Kg | 600 Kg | 600 Kg | 600 Kg | 100 Kg | 100 Kg |
| LHG | 73.5 g | 4.33 Kg | 4.36 Kg | 4.81 Kg | 765.0 g | 748.2 g |
| yield* | 0.74% | 0.72% | 0.73% | 0.80% | 0.77% | 0.75% |

*LHG in table 1 does not include the reserved samples in HG stage.

Embodiment 2: Physicochemical and Biological Properties of LHG

Provided by the present embodiment is physicochemical and biological properties of LHG prepared in embodiment 1.
1. Materials
Test compound: LHG prepared in embodiment 1.
2. Method
(1) Weight-Average Molecular Weight
The LHG was subjected to GPC-HPLC analysis. Two columns were used for weight-average molecular weight analysis TSKgel G2000SW (7.8 mm×30 cm, 5 μm) and TSKgel G3000SW (7.8 mm×30 cm, 5 μm). The detector was a differential refractive index detector (RID). The standard for weight-average molecular weight calculation was the weight-average molecular weight calibration RS of USP commercial low molecular weight heparin. The analysis software included HPLC workstation and Agilent's GPC software, wherein SEC-HPLC was used for analysis and determination, and GPC software was used for computing.
(2) Anti-Xa Factor Activity
Anti-Xa factor activity was determined referring to USP40 (titer detection method for heparin sodium factor).
(3) Anticoagulation Activity
Anticoagulation activity was determined referring to USP32 (titer detection method for heparin sodium, sheep plasma method).

(4) Sodium Content

Sodium content was determined referring to Chinese Pharmacopeia 0406 (atomic ab sorption spectrophotometry).

(5) Mole Ratio of GlcA:GalNAc:Fuc

GlcA content was determined by carbazole method, GalNAc content was determined by Elson-Morgon method, the mole ratio of GalNAc:Fuc was calculated according to integral area of $^1$H NMR methyl-peak.

(6) Ratio of Sulfate Radical:Carboxylate Radical

Ratio of sulfate radical:carboxylate radical was determined by conductometric titration method.

(7) Specific Optical Rotation

Specific optical rotation was determined referring to Chinese Pharmacopeia (2010, appendix part two, VIE method).

(8) Absolute Weight-Average Molecular Weight

Absolute weight-average molecular weight was determined by SEC-MALLS method.

3. Results

Physicochemical and biological properties of LHG of the present embodiment are presented in Table 2.

3) Sodium content of LHG from different batches is approximate, is 11.2-12.1%. And sodium content matches with the number of carboxyl group and sulfate radical in constitutional unit. Sodium is bonded to these groups by ionic bonds.

4) Mole ratio of GlcA:GalNAc:Fuc of LHG from different batches is approximate, is 1:(0.8-1.2):(0.6-1.2).

5) Ratio of sulfate radical:carboxylate radical of LHG from different batches is approximate, is 3.9-4.1. The result indicates that there are 4.0 sulfate radical modification in one constituent unit (GlcA(Fuc)-GalNAc), and sulfate radical content is high.

6) Specific optical rotation of LHG from different batches is −47°~−55°.

Embodiment 3: Structural Characteristics of Disaccharide Unit in Backbone of LHG Provided by the present embodiment is structural characteristics of disaccharide unit in backbone of LHG prepared in embodiment 1.

TABLE 2

| Test | LHG-L180501 | LHG-181101 | LHG-181102 | LHG-181103 | LHG-190301 | LHG-190501 |
|---|---|---|---|---|---|---|
| Weight-average molecular weight | 7200 Da | 8550 Da | 8100 Da | 7550 Da | 9200 Da | 7850 Da |
| Anti-Xa factor activity | 1.1 U/mg | 0.7 IU/mg | 0.7 IU/mg | 0.9 IU/mg | 1.0 IU/mg | 0.6 IU/mg |
| Anticoagulation activity (sheep Plasma method) | 7.9 U/mg | 8.3 U/mg | 8.1 U/mg | 7.5 U/mg | 9.0 U/mg | 8.2 U/mg |
| Sodium content | 12.1% | 11.6% | 12.0% | 11.2% | 11.6% | 11.5% |
| Mole ratio of GlcA: GalNAc:Fuc | 1.00:1.02:0.82 | 1.00:1.03:0.84 | 1.00:0.87:1.09 | 1.00:1.01:0.69 | 1.00:0.97:0.91 | 1.00:1.12:1.13 |
| Ratio of sulfate radical: carboxylate radical | 3.9 | 4.0 | 4.2 | 4.1 | 4.1 | 4.0 |
| Specific optical rotation | −47.2° | −54.0° | −52.4° | −51.0° | −48.6° | −50.6° |

As shown is Table 2:

1) The weight-average molecular weight of LHG from different batches is all below 10000 Da, but the weight-average molecular weight of natural HG is usually above 60000-80000 Da. The result indicates that LHG belongs to low-molecular-weight depolymerized holothurian glycosaminoglycan.

Furthermore, absolute weight-average molecular weight determined by SEC-MALLS method shows that the maximum molecular component of LHG is 28000-30000 Da. According to the speculation of repeating saccharide unit (GlcA(Fuc)-GalNAC) and corresponding sulfate degree modification (4.0, Ratio of sulfate radical:carboxylate radical), in the formula of said low-molecular-weight holothurian glycosaminoglycan, the maximum of n is 32.

2) Almost negligible anti-Xa activity of LHG from different batches shows that anticoagulant function does not depend on anti-Xa factor, and realized in other way. Anticoagulation activity by sheep plasma method is also below 10 U/mg. The results indicate that LHG has low anticoagulation activity.

According to the previous literatures, natural HG is a glycosaminoglycan (GAG), in the constituent unit of HG, glucuronic acid (GlcA) and N-acetylaminogalactose (GalNAc) are interconnected to form a chondroitin sulfate (CS) backbone of a disaccharide repeating structural unit, and sulfate fucose (Fuc) is connected to the backbone as a side chain. LHG belongs to low-molecular-weight depolymerized natural HG, which has the similar essential characteristics with natural HG. However, LHG has many forms because the degree and position of sulfate or acetyl group substitution are different in disaccharide repeating structural unit (dp2) in backbone. Chondroitin sulfate enzyme can't degrade the chondroitin sulfate backbone of LHG, and thus can't complete the disaccharide analysis of the backbone because of fucose side chain. In this embodiment, firstly fucose side chain was removed gradually by weak acid acidolysis, and then the backbone was enzymolized thoroughly with chondroitin sulfate lyase ABC, finally disaccharide unit was released, disaccharide analysis was conducted.

1. Materials

Test compound: LHG (batch number is LHG-L180501) prepared in embodiment 1.

Reagent: 8 CS disaccharide (dp2) standards (No. C3202) purchased from Beijing Adhaoke Technology Co., LTD, chondroitin sulfate lyase ABC (No. 120M4095V) purchased from Sigma, other reagents were analytically pure.

2. Method 2.1 Sample Preparation 2.1.1 Fucose Side Chain was Removed by Different Degree of Acidolysis 192.0 mg of LHG was dissolved thoroughly in 4.8 mL of 0.1M $H_2SO_4$ removed with 1000 μL of pipette, and 40 mg/mL LHG solution was obtained. The LHG solution was divided equally into six groups, name as Sample 1, Sample 2, Sample 3, Sample 4, Sample 5 and Sample 6, then the six samples were transferred into oil bath at 100° C. for being degraded. The time of Sample 1-6 removed from oil bath is 0 min, 30 min, 60 min, 90 min, 120 min, 240 min. Every sample was cooled to room temperature, then was adjusted pH to 7.0 with $Ba(OH)_2$ saturated solution. The neutral sample was centrifuged, and the precipitates were removed. For every sample, ⅓ of the supernatant was transferred into a 500 Da dialysis bag, then dialyzed for 24 h. The dialyzed sample was transferred into a weighed centrifugal tube, freeze dry to reserve.

2.1.2 Disaccharide Unit was Obtained by Enzymolysis with Chondroitin Sulfate Lyase ABC Every said dry acidolysis sample was dissolved thoroughly in 50 mM Tris-HCl (pH 8.0) to obtain 20 mg/mL sample solution. 50 μL of sample solution was removed into 1 mL centrifuge tube, and 0.2 IU (0.1 IU/10 μL) of chondroitin sulfate lyase ABC was dissolved thoroughly in the sample solution. The sealed 1 mL centrifuge tube was putted in 37° C. constant temperature water bath, and the sample solution was enzymolized for 36 h to obtain disaccharide unit. The six enzymolized samples name as Sample 1-M, Sample 2-M, Sample 3-M, Sample 4-M, Sample 5-M and Sample 6-M, and were analyzed by Agilent 1260 Infinity liquid chromatograph.

2.2 SAX-UV Analysis

Instrument: Agilent 1260 Infinity liquid chromatograph.

Column: Welch Ultimate XB-SAX (4.6×250 mm, 3.0 μm).

Mobile phase A: 2.33 mM $NaH_2PO_4.2H_2O$, pH 3.0 (0.364 g of $NaH_2PO_4.2H_2O$ was dissolved in 950 mL of purified water to obtain $NaH_2PO_4.2H_2O$ solution, $NaH_2PO_4.2H_2O$ solution was set volume to 1 L with purified water, then adjusted pH to 3.0 with $H_3PO_4$, and filtered with 0.22 μm membrane, finally degassed to reserve).

Mobile phase B: 1.143 M $NaClO_4.H_2O$, pH 3.0 (160.6044 g of $NaClO_4.H_2O$ was dissolved in 950 mL of the mobile phase A to obtain mixture, the mixture was set volume to 1 L with the mobile phase A, then adjusted pH to 3.0 with $H_3PO_4$, and filtered with 0.22 μm membrane, finally degassed to reserve).

Flow velocity: 0.6 mL/min.

Column temperature: 45° C.

Injection volume: 5 μL.

Detection wavelength: 232 nm.

Gradient elution is presented in Table 3.

TABLE 3

| Time/min | Mobile phase A/% | Mobile phase B/% |
|---|---|---|
| 0 | 97 | 3 |
| 100 | 65 | 35 |

TABLE 3-continued

| Time/min | Mobile phase A/% | Mobile phase B/% |
|---|---|---|
| 120 | 0 | 100 |
| 130 | 0 | 100 |
| 135 | 97 | 3 |

3. Results

Figure 1B:
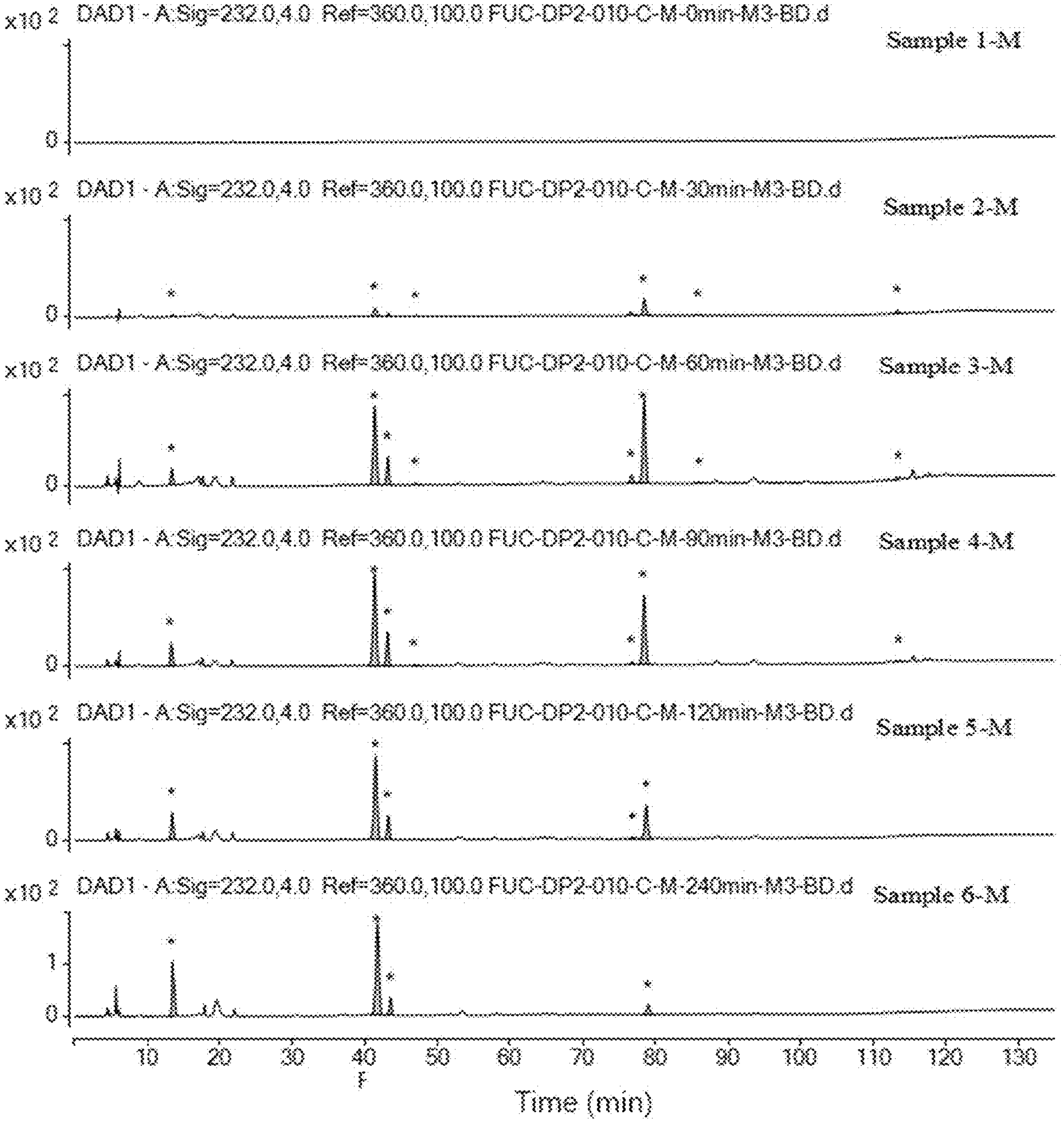

HPLC results of structural characteristics of disaccharide repeating structural unit in backbone of LHG provided by embodiment 3 of the present invention are shown in FIG. 1. Wherein the results of the disaccharide standards are shown in FIG. 1 (A), the results of Sample 1-M, Sample 2-M, Sample 3-M, Sample 4-M, Sample 5-M and Sample 6-M are shown in FIG. 1 (B).

Because there is unsaturated double bond on the position 4,5 of the disaccharide unit after enzymolysis, strong anion exchange chromatography cascaded UV detector was used for detection (referring to SAX-UV in 2.2).

In order to ensure the feasibility of the method, firstly 8 CS disaccharide (dp2) standards were separated with SAX-UV method referring to 2.2, the results are shown in FIG. 1 (A). As shown in FIG. 1 (A), 8 CS disaccharide (dp2) standards can be separated effectively, Peak A-H is ΔUA→GalNAc, ΔUA→GalNAc,6S, ΔUA→GalNAc,4S, ΔUA,2S→GalNAc, ΔUA,2S→GalNAc,6S, ΔUA→GalNAc,4S,6S, ΔUA,2S→GalNAc,4S, ΔUA,2S→GalNAc,4S,6S disaccharide in turn.

Above-mentioned samples with different degree of acidolysis were enzymolized for 36 h under the same enzymolysis conditions. Sample 1-M, Sample 2-M, Sample 3-M, Sample 4-M, Sample 5-M and Sample 6-M were analyzed by SAX-UV, the results are shown in FIG. 1 (B). As shown in FIG. 1 (B), Enzymolysis effect of chondroitin sulfate when fucose side chain wasn't removed by no acidolysis is bad, disaccharide wasn't detected in Sample 1-M. This indicates that LHG with Fuc side chain cannot be enzymolized. When the time of acidolysis is 30 min, the LHG with Fuc side chains partly removed can be enzymolized to release 8 kinds of CS disaccharides, but the content of every disaccharide is small in Sample 2-M, enzymolysis effect is also bad. When the time of acidolysis is 60 min, the backbone of LHG can be better enzymolized to release 8 kinds of CS disaccharides, the content of every disaccharide increases in Sample 3-M. When the time of acidolysis is 90 min (Sample 4-M), enzymolysis efficiency is maximum in six samples. When the time of acidolysis is 120 min (Sample 5-M) and 240 min (Sample 6-M), enzymolysis efficiency decreases gradually.

In addition, as the previous operation and preparation conditions of each sample are same completely, enzymolysis effect can be determined by the variation of peak area on the premise of the same determination conditions.

Figure 2A:
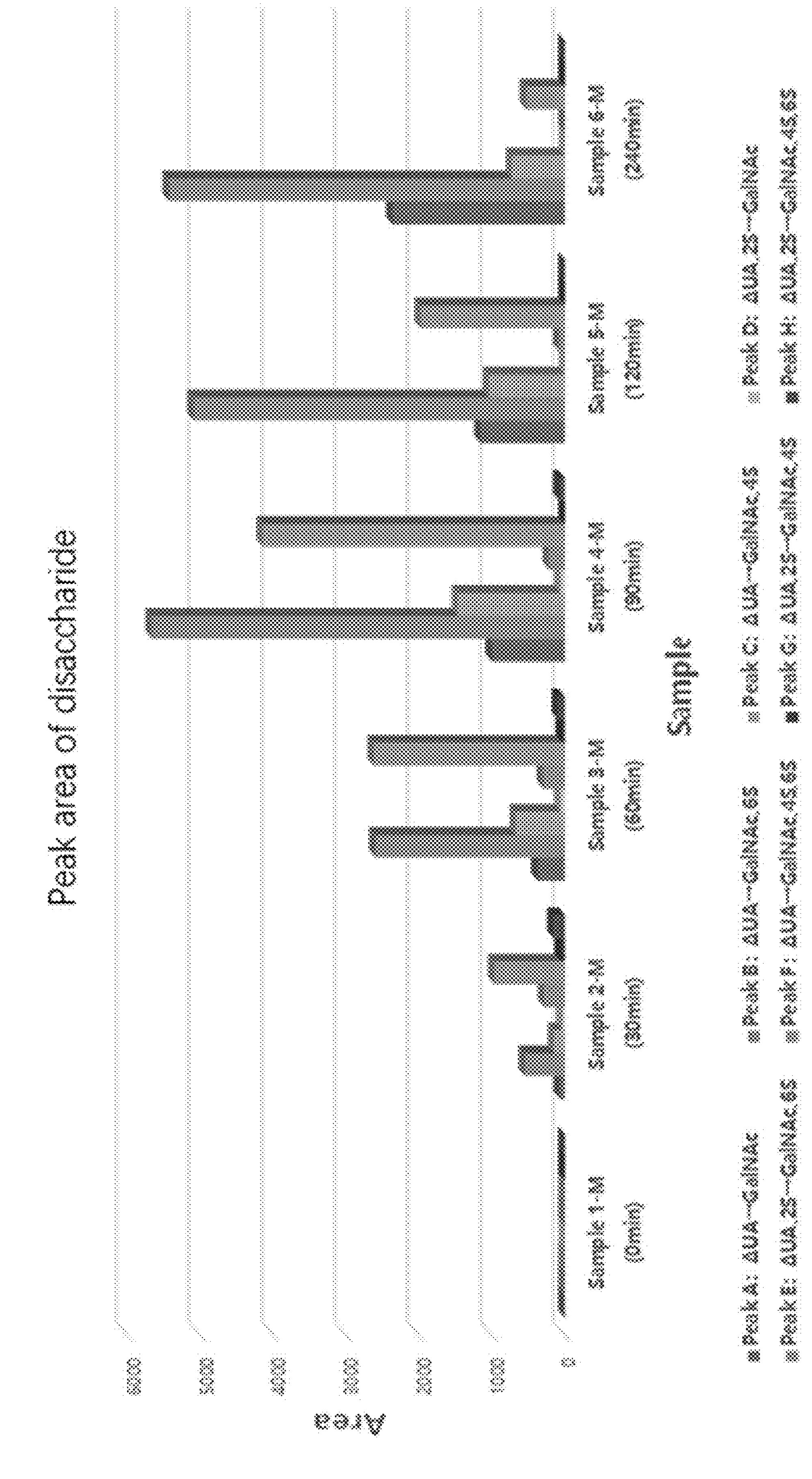
FIG. 2 is histograms of peak area and peak area percentage of the disaccharide in every sample provided by embodiment 3 of the present invention, wherein the histogram of peak area of the disaccharide is shown in FIG. 2 (A), histogram of peak area percentage of the disaccharide is shown in FIG. 2 (B).
Figure 2B:
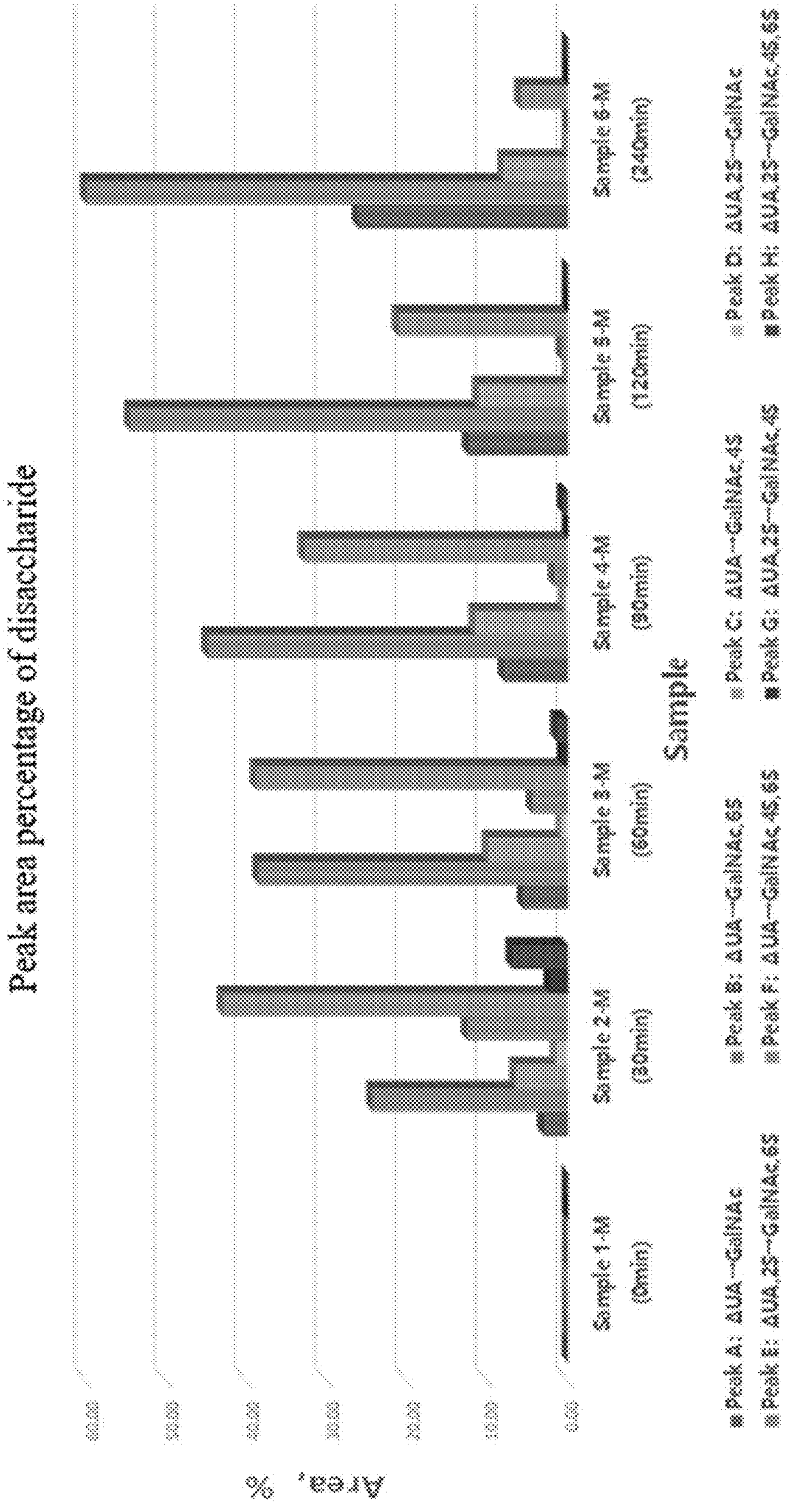

Histograms of peak area and peak area percentage of the disaccharide in every sample provided by embodiment 3 are shown in FIG. 2. Wherein the histogram of peak area of the disaccharide is shown in FIG. 2 (A), histogram of peak area percentage of the disaccharide is shown in FIG. 2 (B). In the FIG. 2 (A) and FIG. 2 (B), the histogram of every sample contains 8 columns, these 8 columns represent ΔUA→GalNAc, ΔUA→GalNAc,6S, ΔUA→GalNAc,4S, ΔUA,2S→GalNAc, ΔUA,2S→GalNAc,6S, ΔUA→GalNAc,4S,6S, ΔUA,2S→GalNAc,4S and ΔUA,2S→GalNAc,4S,6S from left to right.

As shown in FIG. 2 (A), if only the total amount of disaccharide is evaluated, the evaluated result shows 90 min is the best acidolysis time.

As shown in FIG. 2 (B), the percentage of every disaccharide in sample is analyzed, the analysis result shows the percentage of every disaccharide in sample changes gradually over acidolysis time, and the variation trend of every disaccharide was not same completely. The percentage of no sulfate disaccharide (ΔUA→GalNAc) and 6-sulfate disaccharide (ΔUA→GalNAc,6S) increases gradually over acidolysis time. The percentage of 4-sulfate disaccharide (ΔUA→GalNAc,4S) increases at first and then decreases, the percentage is highest when acidolysis time is 90 min. The percentage of 2-sulfate disaccharide (ΔUA,2S→GalNAc) decreases gradually over acidolysis time, cannot be detected when acidolysis time is 120 min. The percentage of disulfate disaccharide ΔUA,2S→GalNAc,6S, ΔUA→GalNAc,4S,6S, ΔUA,2S→GalNAc,4S and trisulfate disaccharide ΔUA,2S→GalNAc,4S,6S decreases gradually over acidolysis time. These results indicate Fuc side chain can removed by appropriate acidolysis, the enzyme action site of the disaccharide unit in the backbone is exposed, which benefit to enzymolysis and analysis of the backbone, so the content of components after enzymolysis increases. It can be seen from the increasing of low-sulfate disaccharide content in enzymolysis components, if the time of acidolysis is too long, Fuc side chain is removed, at the same time the exposed backbone is also acid-hydrolyzed, which induces sulfate radical falling off. When the time of acidolysis is too long, ΔUA,2S→GalNAc, ΔUA,2S→GalNAc,6S, ΔUA,2S→GalNAc,4S and ΔUA,2S→GalNAc,4S,6S even cannot be detected, which influences on the determination and analysis of true disaccharide results.

4. Conclusion and Discussion

Through research and analysis, the types of disaccharide unit in the backbone of the LHG (batch number is LHG-L180501) prepared in embodiment 1 are ΔUA→GalNAc, ΔUA→GalNAc,6S, ΔUA→GalNAc,4S, ΔUA,2S→GalNAc, ΔUA,2S→GalNAc,6S, ΔUA→GalNAc,4S,6S, ΔUA,2S→GalNAc,4S and ΔUA,2S→GalNAc,4S,6S, All eight common disaccharides are exist. In terms of composition ratio of the disaccharide unit, the main is ΔUA→GalNAc, ΔUA→GalNAc,6S, ΔUA→GalNAc,4S and ΔUA→GalNAc,4S,6S. The backbone of the LHG appears a similar structure with chondroitin sulfate E.

Wherein ΔUA,2S (namely GlcA2S in backbone) in the backbone of the LHG isn't reported by the prior art so far. According to analysis result of different degree acidolysis-enzymatic, in the LHG (batch number is LHG-L180501), the percentage of GlcA2S in total GlcA is 10-25%. In this embodiment, samples with different acidolysis degree were analyzed, the results show Fuc side chain of LHG can be removed by gentle acidolysis, and the efficiency of enzymolysis increases. Appearance of Fuc-GalNAc, GlcA-GalNAc and GlcA-GalNAc-Fuc with different sulfate degree shows the exposed backbone of LHG is also acid-hydrolyzed, and the acidolysis degree of exposed backbone of LHG increases with the acidolysis time increasing.

In the same way, other batches LHG prepared in embodiment 1 (include LHG-L180501, LHG-181101, LHG-181103, LHG-190301 and LHG-190501) were conducted the same acidolysis, enzymolysis and SAX-UV analysis. The results show disaccharides in backbone of every said LHG are similar with those of the LHG (batch number is LHG-L180501), and all LHG contains similar ΔUA,2S (namely GlcA2S), the content of GlcA2S is 10-30%. These structure characteristics indicate that LHG is not only the chondroitin sulfate E analogue, but also is the chondroitin sulfate D analogue because the existing of GlcA2S, which has not been reported in literature.

Embodiment 4: $^1$H-NMR of LHG

Provided by the present embodiment is $^1$H-NMR of LHG prepared in embodiment 1, structural characteristics of LHG were analyzed by $^1$H-NMR.

1. Test compound: LHG (batch number is LHG-L180501) prepared in embodiment 1.

2. Sample preparation: 35 mg of LHG was dissolved thoroughly in 0.6 mL of $D_2O$ (0.002% TSP was added into $D_2O$, as internal calibration zero) to obtain $D_2O$ solution of LHG. The $D_2O$ solution of LHG was transferred into 5 mm NMR tube, then ultrasound treated for 2 min.

3. Instrument: NMR Bruker AC500HD.

4. Software: Bruker Top Spin 3.2 (Bruker Biospin GmbH)

Figure 3A:
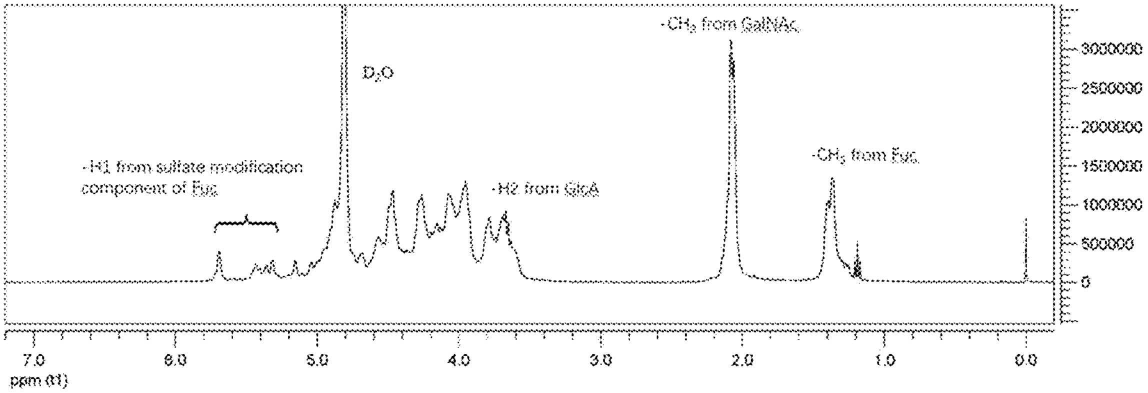
FIG. 3 is $^1$H-NMR spectrum of LHG provided by embodiment 4 of the present invention.
Figure 3B:
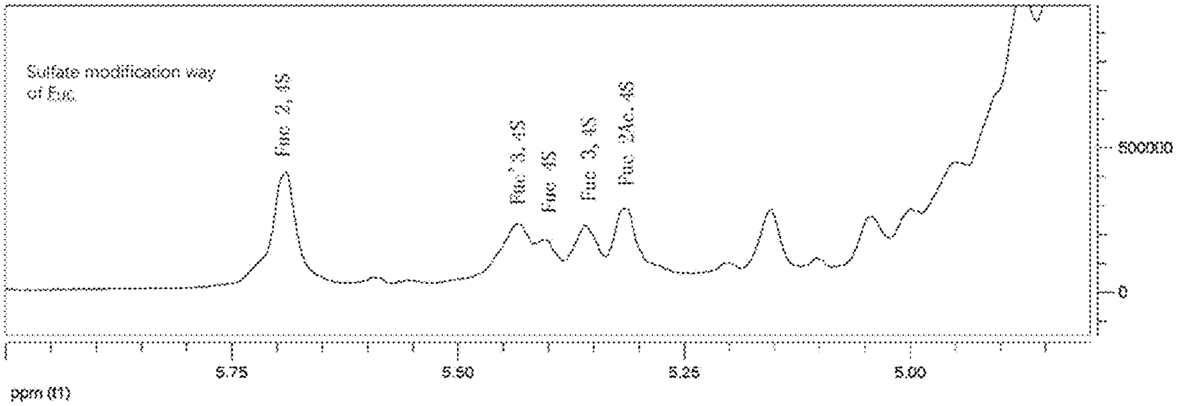

5. Results $^1$H-NMR spectrum of LHG provided by embodiment 4 of the present invention is shown in FIG. 3. Wherein the full $^1$H-NMR spectrum is shown in FIG. 3 (A), the larger $^1$H-NMR spectrum of the sulfate modified part of Fuc is shown in FIG. 3 (B).

As shown in FIG. 3 (A) and FIG. 3 (B), 1.40 ppm is the characteristic peak of methyl group from fucose group (Fuc), 2.08 ppm is the characteristic peak of acetyl methyl group from N-acetylaminogalactosyl group (GalNAc), 3.60 ppm is the characteristic peak of H2 from glucuronic acid group (GlcA), 5.30-5.70 ppm is the characteristic peak of H1 from every sulfate modification component of fucose group (Fuc).

Thus, it can be seen $^1$H-NMR spectrum of LHG provided by the present invention is similar with that of fucose glycosaminoglycans reported in the literature (Paulo A S. et al., J. Biol. Chem., 1996, 271: 23973), structure characteristic of LHG is that the chondroitin sulfate backbone of glucuronic acid group-N-acetylaminogalactosyl group (GlcA-GalNAc) is modified by fucose group (Fuc).

Embodiment 5: Structure Characteristics of LHG by NMR

Modern nuclear magnetic resonance technology, especially two-dimensional nuclear magnetic resonance (HQC-NMR), has been widely used to analyze the structural information of polysaccharide components. Not only it can analyze the signal of the heterohead peak, but also the signal of the ring structure of the saccharide chain. Provided by the present embodiment is the structure characteristics of the saccharide chain of LHG prepared in embodiment 1.

1. Test compound: LHG (batch number is LHG-L190301) prepared in embodiment 1.

2. Sample preparation: 35 mg of LHG was dissolved thoroughly in 0.6 mL of $D_2O$ (0.002% TSP was added into $D_2O$, as internal calibration zero) to obtain $D_2O$ solution of LHG. The $D_2O$ solution of LHG was transferred into 5 mm NMR tube, then ultrasound treated for 2 min. Another sample was prepared by the same way, only the weight of LHG is 100 mg.

3. Instrument: NMR Bruker AC500HD.

4. Software: Bruker Top Spin 3.2 (Bruker Biospin GmbH)

5. Results

Figure 4:
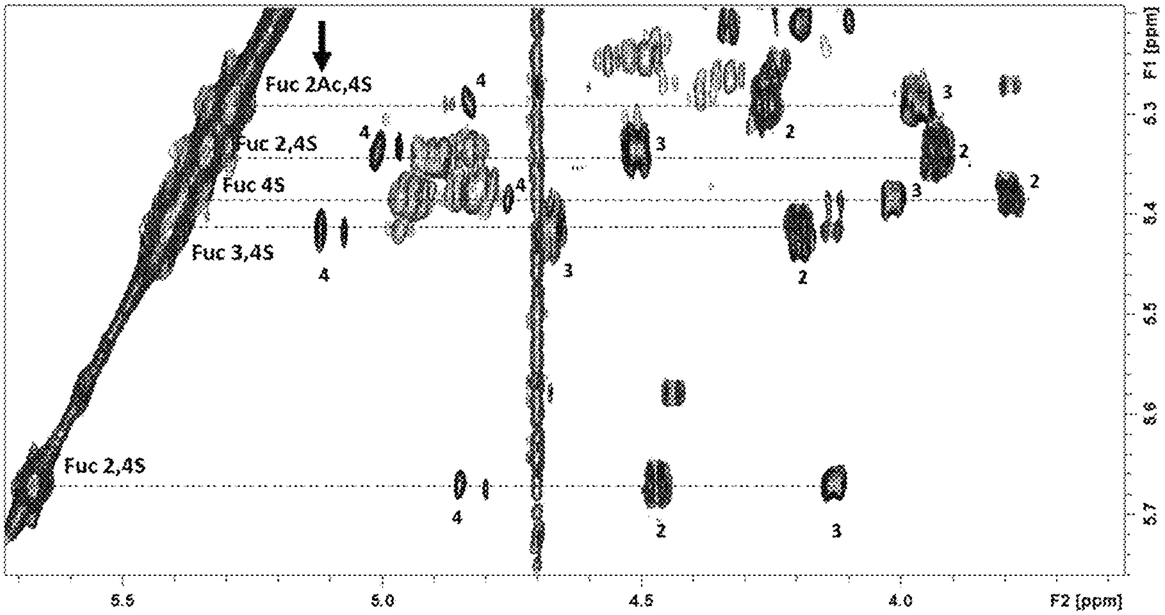
FIG. 4 is superimposed spectrogram of the peak of heterohead COSY and TCOSY of LHG provided by embodiment 5 of the present invention.

Superimposed spectrogram of the peak of heterohead COSY and TCOSY of LHG provided by embodiment 5 of the present invention is shown in FIG. 4. Superimposed spectrogram of the peak of HSQC-COSY and HSQC- TOCSY of LHG provided by embodiment 5 of the present invention is shown in FIG. 5.

Figure 5:
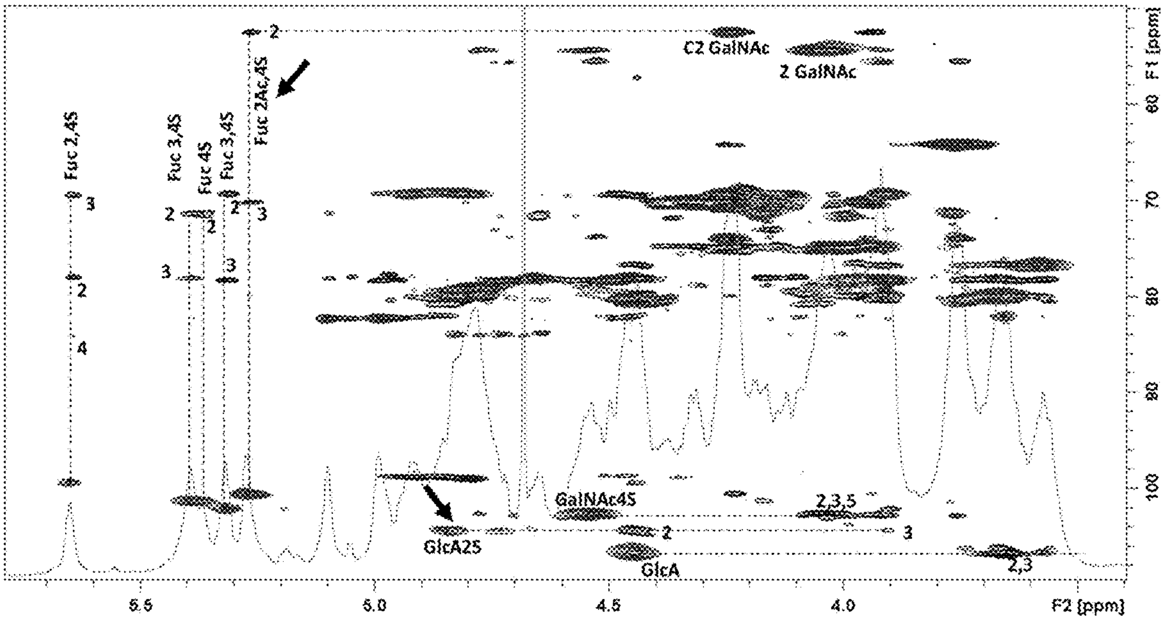
FIG. 5 is superimposed spectrogram of the peak of HSQC-COSY and HSQC-TOCSY of LHG provided by embodiment 5 of the present invention.

As shown in in FIG. 4 and FIG. 5, there are five kinds of fucose group (Fuc) with different sulfate modification ways. Except the conventional 2,4-disulphate ester (Fuc2/4S), two kind of 3,4-disulphate ester (Fuc3/4S and Fuc'3/4S) and 4-sulphate ester (Fuc4S), 5.28/100.5 ppm is the characteristic signal from another sulfate modification Fuc, and 4.26/52.3 ppm is the characteristic signal from H2/C2, these characteristic signals of Fuc is similar with those of acetylation modification, so the sulfate modification Fuc is Fuc2Ac4S. Single signal 4.85/104.3 ppm and 4.4/80.1 ppm of H2/C2 indicate there is sulfate modification on the 2-O position of GlcA (GlcA2S).

The above results indicate there are acetylation modification on the 2-O position of Fuc (Fuc2Ac) and sulfate modification on the 2-O position of GlcA (GlcA2S).

Figure 6:
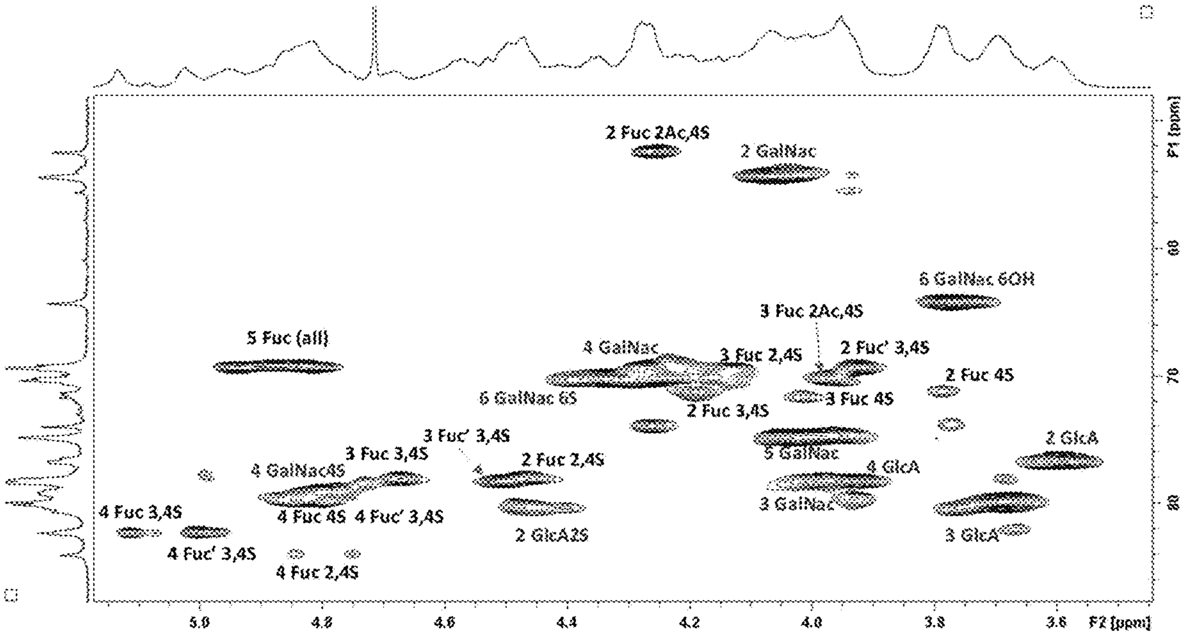
FIG. 6 is HSQC spectrogram of the polysaccharide ring of LHG provided by embodiment 5 of the present invention.

HSQC spectrogram of the saccharide ring of LHG provided by embodiment 5 of the present invention is shown in FIG. 6.

As shown in in FIG. 6, other structure characteristics of LHG contain partial sulfation on the 6-O position of GalNAc, shown in 70.3 ppm of C6S (GalNAc6S) and 64.3 ppm of C6OH (GalNAc).

Furthermore, on a molar ratio basis, the ratio of GlcA:GalNAc:Fuc is 1:1:0.9, which integral calculated by HSQC or $^{13}C$ spectrogram, and the results by the two spectrograms is consistent.

Attribution of each signal are presented in FIG. 6, Table 4, and Table 5.

TABLE 4

| Saccharide unit | % | $^1H$ NMR (ppm) 1 | 2 | 3 | 4 | 5 | 6 |
|---|---|---|---|---|---|---|---|
| GlcA | 80 | 4.46 | 3.60 | 3.69 | 3.93 | 3.69 | / |
| GlcA2S | 20 | 4.85 | 4.46 | / | / | / | / |
| GalNAc, 4, 6S | / | 4.57 | 4.05 | 4.02 | 4.82 | 4.0 | 4.2-4.3 |
| Fuc2, 4S | 15 | 5.68 | 4.47 | 4.13 | 4.84 | 4.83-4.94 | 1.35-1.40 |
| Fuc3, 4S | 26 | 5.43 | 4.20 | 4.68 | 5.12 | 4.83-4.94 | 1.35-1.40 |
| Fuc4S | 10 | 5.39 | 3.79 | 4.01 | 4.76 | 4.83-4.94 | 1.35-1.40 |
| Fuc'3, 4S | 21 | 5.35 | 3.93 | 4.51 | 5.00 | 4.83-4.94 | 1.35-1.40 |
| Fuc2Ac, 4S | 27 | 5.28 | 4.26 | 3.97 | 4.83 | 4.83-4.94 | 1.35-1.40 |

TABLE 5

| Saccharide unit | $^{13}C$ NMR (ppm) 1 | 2 | 3 | 4 | 5 | 6 |
|---|---|---|---|---|---|---|
| GlcA | 106.5 | 76.6 | 79.9 | 78.2 | 79.9 | 177.7 |
| GlcA2S | 104.3 | 80.1 | / | / | / | / |
| GalNAc, 4, 6S | 102.6 | 54.3 | 78.0 | 79.2 | 74.8 | 70.0 |
| Fuc2, 4S | 99.3 | 77.9 | 69.3 | 84.0 | 69.2 | 18.6-18.9 |
| Fuc3, 4S | 101.2 | 71.3 | 78.1 | 82.2 | 69.2 | 18.6-18.9 |
| Fuc4S | 101.2 | 71.2 | 71.7 | 79.6 | 69.2 | 18.6-18.9 |
| Fuc'3, 4S | 102.0 | 69.2 | 78.3 | 82.2 | 69.2 | 18.6-18.9 |
| Fuc2Ac, 4S | 100.5 | 52.3 | 70.1 | 79.8 | 69.2 | 18.6-18.9 |

By integration of the $^1H$ signal, the percentage of GlcA2S modification in total GlcA is 20%, the percentage is consistent with the result (10-30%) of the acidolysis-enzymolysis analysis in said embodiment 3. There are many kinds of modification ways in Fuc, the percentage of Fuc2Ac4S in total Fuc is 27%.

It can be seen that the LHG disclosed by the present embodiment contains the characteristics of GlcA2S and Fuc2Ac, HG or HG derivatives contains these two structural characteristics has not been reported in the literature.

Embodiment 6: Structure Characteristic of Different Batch LHG by NMR

It is well known that fucosylation chondroitin sulfate analogues of HG or HG derivatives have important biological activities on inflammation, thrombosis and tumor metastasis. HG is obtained by extraction or partial chemical treatment, and there may be structural differences between HG from different sources or batches. In general, the modification characteristics of molecular structure of HG are correlated with their biological functions, this correlation study is very challenging. In the present embodiment, the characteristics and differences of LHG from different sources or batches were analyzed by NMR.

1. Test compound: LHG (batch number is LHG-L180501) prepared in embodiment 1,
   LHG (batch number is LHG-L181101) prepared in embodiment 1,
   LHG (batch number is LHG-L181102) prepared in embodiment 1,
   LHG (batch number is LHG-L181103) prepared in embodiment 1,
   the last three batches are the pilot products of continuous 600 Kg batch.
2. Instrument: NMR Bruker AC500HD.
3. Software: Bruker Top Spin 3.2 (Bruker Biospin GmbH)
4. Results $^1H$-NMR spectrum contrast diagram of LHG provided by embodiment 6 of the present invention is shown in FIG. 7.

Figure 7:
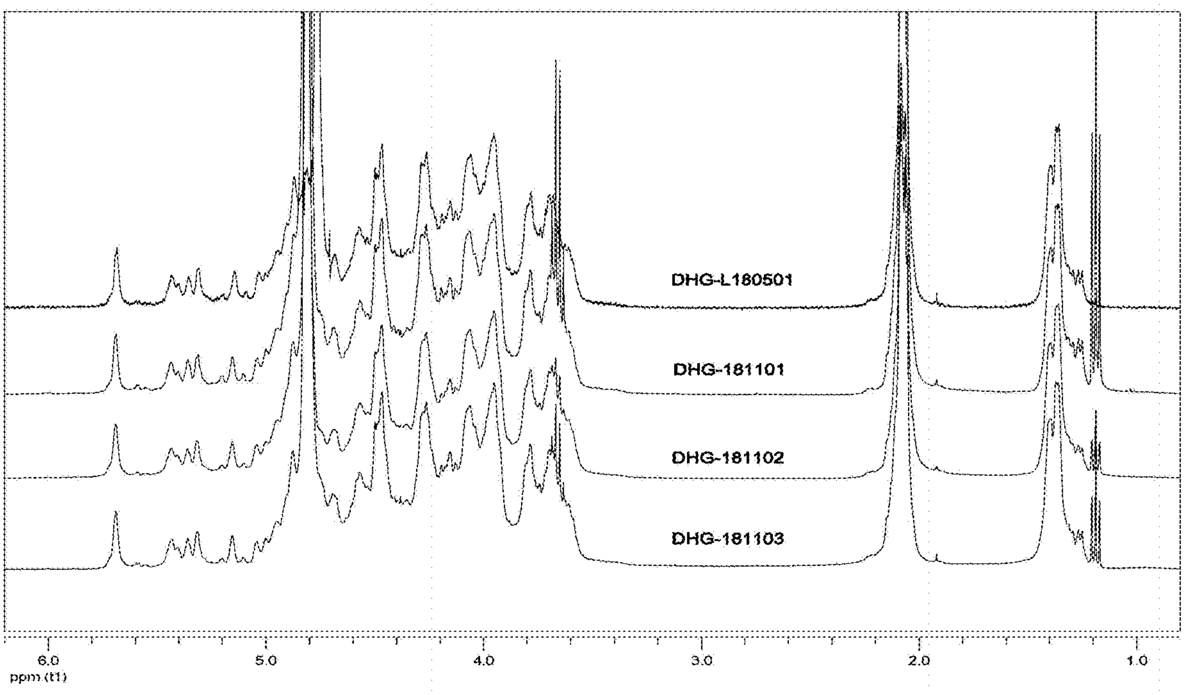
FIG. 7 is $^1$H-NMR spectrum contrast diagram of LHG provided by embodiment 6 of the present invention.

As shown in FIG. 7, the $^1H$-NMR spectrums of these LHG samples are almost identical, wherein 1.2 ppm and 3.6 ppm are signals of the residual solvent ethanol. In FIG. 7, five kinds of Fuc modification can be recognized, which contains Fuc 2,4S, Fuc 3,4S, Fuc 4S, Fuc '3,4S and Fuc 2Ac,4S. The percentage of every Fuc modification can be calculated by integration of the $^1H$ chemical shift according to Table 3 in said embodiment 4. Furthermore, the percentage of especially the 2-O position modification GlcA2S in total GlcA can be obtained by integration of HSQC-NMR signal. The results are presented in Table 6.

TABLE 6

| Batch number | Fuc2, 4S | Fuc3, 4S + Fuc4S | Fuc'3, 4S | Fuc2Ac, 4S | GlcA2S | GlcA/ Fuc |
|---|---|---|---|---|---|---|
| LHG-L180501 | 33% | 26% | 24% | 15% | 23% | 1:0.82 |
| LHG-181101 | 37% | 26% | 24% | 13% | 25% | 1:0.71 |
| LHG-181102 | 36% | 27% | 23% | 14% | 24% | 1:0.75 |
| LHG-181103 | 32% | 25% | 24% | 19% | 20% | 1:0.80 |

It can be seen that said batch LHG disclosed by the present embodiment contains the structural characteristics of GlcA2S (the percentage of GlcA2S is 20-25%) and Fuc2Ac (the percentage of Fuc2Ac,4S is 13-19%), HG or HG derivatives containing these two structural characteristics has not been reported in the literature.

Embodiment 7: Structure Characteristic of Different Weight-Average Molecular Weight Components in LHG by NMR In the present embodiment, firstly different weight-average molecular weight components in LHG were obtained by separation of gel permeation chromatography, then structure characteristic of different weight-average molecular weight components in LHG was analyzed by NMR.

Figure 8:
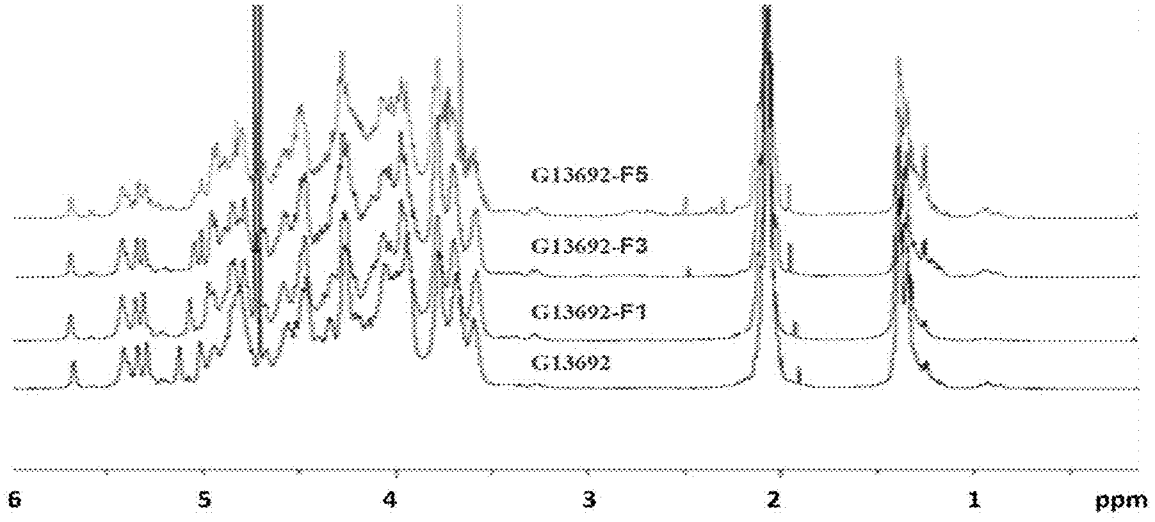
FIG. 8 is $^1$H-NMR spectrum contrast diagram of different weight-average molecular weight components and LHG provided by embodiment 7 of the present invention.

1. Test compound: 1) LHG (batch number is LHG-L190301) prepared in embodiment 1, the weight-average molecular weight is 9200 Da, analysis number is G13692,
   2) Component 1, the weight-average molecular weight is 21400 Da, analysis number is G13692_F1,
   3) Component 2, the weight-average molecular weight is 6600 Da, analysis number is G13692_F3,
   4) Component 3, the weight-average molecular weight is 4300 Da, analysis number is G13692_F5.
2. Instrument: NMR Bruker AC500HD.
3. Software: Bruker Top Spin 3.2 (Bruker Biospin GmbH)
4. Results $^1$H-NMR spectrum contrast diagram of different weight-average molecular weight components and LHG provided by embodiment 7 of the present invention is shown in FIG. 8. As shown in FIG. 8, the $^1$H-NMR spectrums of these different weight-average molecular weight components are almost identical, although the weight average molecular weight of different components is large different. Wherein G13692_F3 and G13692_F5 components show better resolution, while G13692_F1 and G13692 show worse resolution, which attributed to the difference of molecular weight and dispersion of component. Meanwhile, HSQC-NMR spectrums of these components were also obtained, the result is consistent with that of $^1$H-NMR spectrum.

In FIG. 8, five kinds of Fuc modification can be recognized, which contains Fuc 2,4S, Fuc 3,4S, Fuc 4S, Fuc '3,4S and Fuc 2Ac,4S. The percentage of every Fuc modification can be calculated by integration of the $^1$H chemical shift according to Table 4 in said embodiment 5. Furthermore, the percentage of especially the 2-O position modification GlcA2S in total GlcA can be obtained by integration of HSQC-NMR signal. The results are presented in Table 7.

TABLE 7

| Batch number | Fuc2, 4S | Fuc3, 4S + Fuc4S | Fuc'3, 4S | Fuc2Ac, 4S | GlcA2S | GlcA/ Fuc |
|---|---|---|---|---|---|---|
| G13692 | 13% | 27% | 33% | 27% | 20% | 1:0.82 |
| G13692_F1 | 12% | 28% | 38% | 23% | 18% | 1:0.85 |
| G13692_F3 | 16% | 35% | 26% | 23% | 20% | 1:0.79 |
| G13692_F5 | 19% | 30% | 30% | 19% | 23% | 1:0.91 |

It can be seen that said different weight-average molecular weight components in LHG disclosed by the present embodiment contain the structural characteristics of GlcA2S (the percentage of GlcA2S is 18-23%) and Fuc2Ac (the percentage of Fuc2Ac,4S is 19-27%), HG or HG derivatives containing these two structural characteristics has not been reported in the literature.

Embodiment 8: Inducing Platelet Aggregation Activity of LHG

Provided by the present embodiment is the analysis experiment of LHG inducing platelet aggregation activity.

As is known to all, platelet hyperfunction is closely related to cardiovascular disease, blood clots and tumor, the effect of platelet receives more and more recognition in the field of these diseases. The results of experiment in vitro of many clinical anti-cardiovascular drugs, antithrombotic drugs even antitumor drugs indicate that these clinical drugs can inhibit platelet function, such as platelet aggregation. Influence of LHG on arachidonic acid (AA) inducing platelet aggregation in rabbit was investigated in the present embodiment.

1. Materials

Test compound: LHG (batch number is LHG-L180501) prepared in embodiment 1, HG (pure product, batch number is HG-L180501 retained sample of HG in the step 1 during preparation of LHG-L180501 in embodiment 1).

2. Method

The rabbit was exsanguinated through carotid artery, and blood was collected in a silicified centrifuge tube. 3.8% sodium citrate was added in blood for anticoagulation, volume ratio is 9:1, then the mixture was centrifugated for 10 min at room temperature (800 r/min), the upper fluid obtained was platelet-rich plasma (PRP). The rest blood was centrifugated for 10 min at room temperature (3000 r/min) to obtain platelet-poor plasma (PPP) as the reference or to regulate the platelet count in PRP. In the experiment, platelet count in PRP was 500-700 thousand.

The final concentration of LHG and HG is 2.4 μg/mL, 12 μg/mL, 60 μg/mL and 300 μg/mL respectively. The platelet aggregation experiment was conducted with an inducer AA (final concentration is 60 μmol/L), and each experiment was repeated 5 times.

Rate of platelet aggregation was measured by turbidimetry, and result was taken the average of the three measurements.

3. Results

Effect of LHG on AA-inducing platelet aggregation in rabbit provided by embodiment 8 of the present invention is presented in Table 8.

As shown in Table 8, LHG sample group has no significant promoting AA-inducing platelet aggregation, except the final concentration of LHG is 300 μg/mL. While all HG sample group has significant promoting AA-inducing platelet aggregation in rabbit, except the lowest concentration (2.4 μg/mL), and the higher the concentration of HG, the stronger the aggregation.

TABLE 8

| | Rate of platelet aggregation ± SD (%) | | | | |
|---|---|---|---|---|---|
| Group | 0 μg/mL | 2.4 μg/mL | 12 μg/mL | 60 μg/mL | 300 μg/mL |
| LHG sample group | 100 ± 18 | 106 ± 19 | 114 ± 21 | 115 ± 27 | 121 ± 26 |
| HG sample group | 100 ± 18 | 115 ± 26 | 133 ± 28* | 143 ± 31* | 151 ± 27** |

Compared with 0 μg/mL,

*is P < 0.05, and

**is P < 0.01

4. Discussion

Reported literatures show that natural macromolecule HG has an anticoagulant function, but this anticoagulant function cannot inhibit platelet aggregation, inversely can induce platelet aggregation. Activation and metabolism of platelet do not occur during aggregation, aggregated platelets cannot play their physiological activity and function. The above experiment results in the present embodiment indicate that macromolecule HG has a significant inducing platelet aggregation activity, especially the platelet aggregation results of high concentration (above 12 μg/mL) have a significant difference with that of the reference (0 μg/mL). While the platelet aggregation results of micromolecular LHG have no statistical difference with that of the reference (0 μg/mL). Therefore, LHG can reduce or even eliminate potential HIT symptom risk, it is better safe.

In addition, the anticoagulant effect of LHG is low, and even though LHG has a weak inducing platelet aggregation activity, it does not induce activate and distortion of the aggregated platelets, so LHG is different from the general inhibitors of platelet functional activity. Therefore, LHG can be used for prevention and treatment for cardiovascular diseases and even tumors.

Embodiment 9: Influences of LHG on Murine Auricle Swelling (Anti-Inflammation Effect)

In this embodiment, an experimental model of xylene inducing murine auricle swelling and inflammation was used to investigate the anti-inflammation effect of LHG.

Inflammation is the resist reaction of living tissue with vascular system to various inflammatory factors, and is the body's immune response to a foreign component. The basic pathological process of inflammation includes metamorphism, exudation and hyperplasia. Manifestations include local redness, swelling, heat, pain, dysfunction, and systemic reactions such as fever, leukocytosis, and monocyte-macrophage system hyperplasia. Excessive inflammatory response will back to bite the body, which causing secondary pathological damage. In addition, inflammation is also involved in the occurrence and development of a variety of diseases, such as rheumatoid arthritis, asthma, neuritis, etc. In recent years, it has also been found that inflammation is closely related to II diabetes, neurodegenerative disease and cancer. It is well known that mucopolysaccharides have certain anti-inflammation effect, for example, heparin can act on acute or chronic inflammation in vivo or in vitro by many ways such as inhibiting selectin. Sodium pentosanosulphate is the only approved drug for clinical interstitial cystitis at present.

1. Materials

Test compound: LHG (batch number is LHG-L180501) prepared in embodiment 1.

Animal: mice, 18-23 g, half male and half female.

2. Method

Drug preparation: LHG was added in ionized water to obtain 100 mg/mL LHG solution. Positive contrast: dexamethasone was added in ionized water to obtain 50 mg/mL dexamethasone solution. Blank contrast: ionized water.

Administration: sub cutaneous injection.

Experimental process: healthy mice are randomly divided into three groups (six in each group, half male and half female), name as LHG drug group, positive control group and blank control group. Three groups' mice were injected with 0.01 mL/1 g of LHG, dexamethasone and ionized water respectively. Drug was administered continuously for 5 days. 30 μL of xylenes was evenly smeared on both sides of the right ear of the mice to induce inflammation at 30 min after the last administration. The left ear was used as the reference. At 1 h after inducing inflammation, mice were executed by removing cervical vertebra. The ear pieces of the same part in the left and right ears were obtained with a hole punter, then the auricle swelling rate and inhibition rate of auricle swelling were calculated by weighing with an analytical balance.

3. Results

The result of LHG inhibition on xylenes inducing murine auricle swelling provided by embodiment 9 of the present invention is presented in Table 9.

TABLE 9

| Group | Auricle swelling rate | Inhibition rate of auricle swelling |
|---|---|---|
| blank control group | 136.4% ± 14.7% | — |
| LHG drug group | 108.6% ± 13.1%* | 20.4% |
| positive control group (dexamethasone) | 102.9% ± 11.3%* | 24.6% |

Compared with blank control group,
*is $P < 0.05$

As shown in Table 9, At 1 h after xylene inducing murine auricle swelling, the degree of auricle swelling decreases in the LHG drug group mice, which is similar with that in the positive control group (dexamethasone) mice, and significantly different from that in the blank control group mice ($P<0.05$). The result indicates that LHG can effectively inhibit the inflammation of murine auricle swelling caused by xylene. Potentially, LHG can be used for treatment of inflammatory diseases.

Embodiment 10: Influences of LHG on Vascular Lesions of Rat's Diabetics Induced by Streptozotocin Model In this embodiment, influences of LHG on vascular lesions of rat's diabetic induced by streptozotocin model was investigated.

Vasculopathy, especially that of diabetic patients, has a high morbidity, which seriously endanger the health and quality of life of patients, and are the primary cause of disability and death in diabetic patients. Mucopolysaccharides are known to play a role in the prevention and treatment of vasculopathy.

1. Materials

Test compound: LHG (batch number is LHG-L180501) prepared in embodiment 1.

Contrast compound: dHG10092, depolymerized holothurian glycosaminoglycan, disclosed in embodiment 2 of the applicant's invention patent CN201510438139.9.

Animal: SD rats, 250±50 g, male.

2. Method

Drug preparation: LHG or dHG10092 was added in ionized water to obtain 100 mg/mL LHG or dHG solution. According to the solid, 30 mg/Kg administration.

Administration: intragastric administration.

Feed ingredients: 1) ordinary fodder: 5% fat, 55% carbohydrates, 23% protein, 17% other components including cellulose and ash. 2) high fat fodder: 50% fat, 17% carbohydrates, 25% protein, 8% other components including cellulose and ash.

Molding and grouping: blank control group of six rats feed ordinary fodder, and the rest twenty-four rats feed high fat fodder. Four weeks later, streptozotocin was injected in one shot (STZ 35 mg/Kg). One week later, tail venous blood of the rats fasting for 12 h was collected, and blood glucose was determined by a glucose meter. Hollow blood glucose (≥16.7 mmol/L) was used as the indicator of successful molding in the diabetic group. The rats of successful molding are randomly divided into three groups (six in each group), name as model control group, LHG drug group, and dHG10092 drug group. The rats of LHG drug group and dHG10092 drug group were given once intragastric administration every day for 12 weeks.

Sample preparation and collection: After 12 weeks of LHG or dHG10092 drug interference, the rats were anesthetized and fixed, their blood was taken. Blood was centrifuged to obtain supernatant which used for the determination of vascular cellular adhesion molecule-1 (VCAM-1), intercellular adhesion molecule-1 (ICAM-1) and nitric oxide (NO). The aortic wall was taken and cryopreserved.

The determination of advanced glycation ends (AGEs) and receptor of advanced glycation end (RAGE) in rat's aorta: 50 mg of aorta tissue dried to constant weight was weighed, then the content of AGEs and RAGE were determined by ELISA method.

3. Results

In diabetes and its models, the generation of AGEs promotes the formation of cross-linking macromolecules of proteins, which damages vascular endothelial cells and induces apoptosis of endothelial cells, resulting in decreasing aortic compliance. AGEs combining with receptors can increase the expression of ICAM-1, VCAM-1, and activate a variety of cytokines to participate in the occurrence of vascular lesion. The increase of NO content in blood is closely related to the increase of vascular permeability, so decreasing NO content can effectively protect vascular endothelial cells, consequently reduce vascular lesion.

Influences of LHG on vascular lesions of rat's diabetic induced by streptozotocin model provided by embodiment 10 of the present invention are presented in Table 10.

As shown in Table 10, compared with blank control group, the rats of model control group after molding: First, the content of AGEs and RAGE in abdominal aorta increases, and has a significant difference (P<0.01), indicating that the AGes-RAGE system in the abdominal aorta of model rats was significantly activated. Second, the content of ICAM-1 and VCAM-1 in serum increases, and also has a significant difference (P<0.01), indicating that the ICAM-1 and VCAM-1 systems of model rats were significantly activated and expressed. Third, the content of NO in serum increases, and has a significant difference (P<0.01).

Compared with model control group, the rats of LHG drug group after intragastric administration: First, the content of AGEs and RAGE in abdominal aorta decreases significantly (P<0.01), indicating that LHG can inhibit significantly the activation of AGes-RAGE system in abdominal aorta of model rats. Second, the content of ICAM-1 and VCAM-1 in serum decreases significantly (P<0.05 or P<0.01), indicating that LHG can inhibit significantly the activation and expression of ICAM-1 and VCAM-1 systems of model rats. Third, the content of NO in serum decreases significantly (P<0.05), indicating that LHG can decrease significantly the content of NO in serum of model rats. In addition, the comparison between dHG10092 drug group and LHG drug group shows that the improvement of LHG on vascular lesion is stronger than that of dHG10092

Furthermore, aortic vascular dyeing and pathology inspection for each group rats found that aortic vascular wall of model control group rats was thickening significantly, lining was not complete, endothelial cells fallen off, vascular smoothmuscle cell was hypertrophic, distorted, and disordered, the number of layers increased, the cell nucleus had different size, cell membrane and nuclear membrane were not clear, cytoplasm was uneven dyeing, there were numerous foam cells and macrophages. However, compared with model control group, the aortic lesions in LHG drug group rats were alleviated significantly, the arrangement of smoothmuscle cell and properties of the cell nucleus were improved significantly, a few foam cells were observed in endothelium, endothelial cells were swelling slightly, and the proliferation of intimal smoothmuscle cell was not obvious.

In a word, LHG can inhibit the activation of AGes-RAGE system in abdominal aorta of model rats, decrease the content of ICAM-1 and VCAM-1 and the content of NO in serum, and alleviate the aortic lesions in rats. The effect of LHG is stronger than that of dHG10092. Potentially, LHG can be used for prevention and treatment of vasculopathy, and pharmaceutical effect of LHG is stronger than that of dHG10092.

TABLE 10

| Group | AGEs (ng/L) | RAGE (ng/L) | VCAM-1 (ng/L) | ICAM-1 (ng/L) | NO (μmol/L) |
| --- | --- | --- | --- | --- | --- |
| Model control group | 277.3 ± 34.2 | 283.6 ± 28.7 | 7.8 ± 1.1 | 6.9 ± 0.9 | 45.3 ± 8.1 |
| LHG drug group | 184.6 ± 21.7** | 196.2 ± 21.5** | 6.6 ± 0.5* | 4.9 ± 0.7** | 31.2 ± 7.2* |
| dHG10092 drug group | 224.6 ± 26.4* | 236.2 ± 24.3* | 7.1 ± 1.0* | 6.0 ± 0.8* | 38.2 ± 7.7* |
| Blank control group | 152.1 ± 13.5** | 158.6 ± 16.2** | 5.1 ± 0.6** | 3.1 ± 0.6** | 19.7 ± 7.4** |

Compared with model control group,
*is P < 0.05,
**is P < 0.01.

Embodiment 11: Influences of LHG on Murine SUIT2-LUC (Human Pancreatic Adenocarcinoma Cell) Lung Metastasis Inhibition Experiment It is well known that sulfated polysaccharides, such as natural HG and low molecular weight heparin, can inhibit the formation and metastasis of a variety of tumors. In this embodiment, the murine lung metastasis model of pancreatic cancer was used to investigate the effect of LHG on anti-tumor or anti-tumor metastasis, and compare with a low molecular weight heparin and dHG disclosed in the applicant's invention patent CN201510438139.9.

1. Materials

Test compound: LHG (batch number is LHG-L180501, the weight-average molecular weight is 7200 Da) prepared in embodiment 1.

Contrast compound 1: dHG10092, depolymerized holothurian glycosaminoglycan, disclosed in embodiment 2 of the applicant's invention patent CN201510438139.9.

Contrast compound 2: Dapheparin sodium, a low molecular weight heparin sodium preparation in the market, the trade name is Fragmin.

Cells: fluorescent labeled SUIT2 cells (SUIT2-LUC, human pancreatic adenocarcinoma cell).

Animal: Athymic nude mice, female.

Instrument: IVIS imaging system, Caliper Life Sciences, Hopkinton, Mass., USA.

2. Method 2.1 Grouping and dose: LHG drug group (LHG-L180501, 30 mg/Kg), dHG control group (dHG10092, 30 mg/Kg), Dapheparin sodium control group (market injection, 10 mg/Kg), negative control group: PBS buffer.

2.2 Administration: subcutaneous injection, single-administration.

2.3 Cell injection and animal management: the mice were injected with 100 μL of human pancreatic adenocarcinoma cell SUIT2-LUC ($1\times10^6$ cells) at the same time of administration, then mice were fed for 2 weeks.

2.4 IVIS imagination: two IVIS imaginations were conducted respectively after mice being injected with human pancreatic adenocarcinoma cell and after mice being fed for 2 weeks.

2.5 Histopathological inspection was conducted at the end of the experiment.

3. Results

Figure 9:
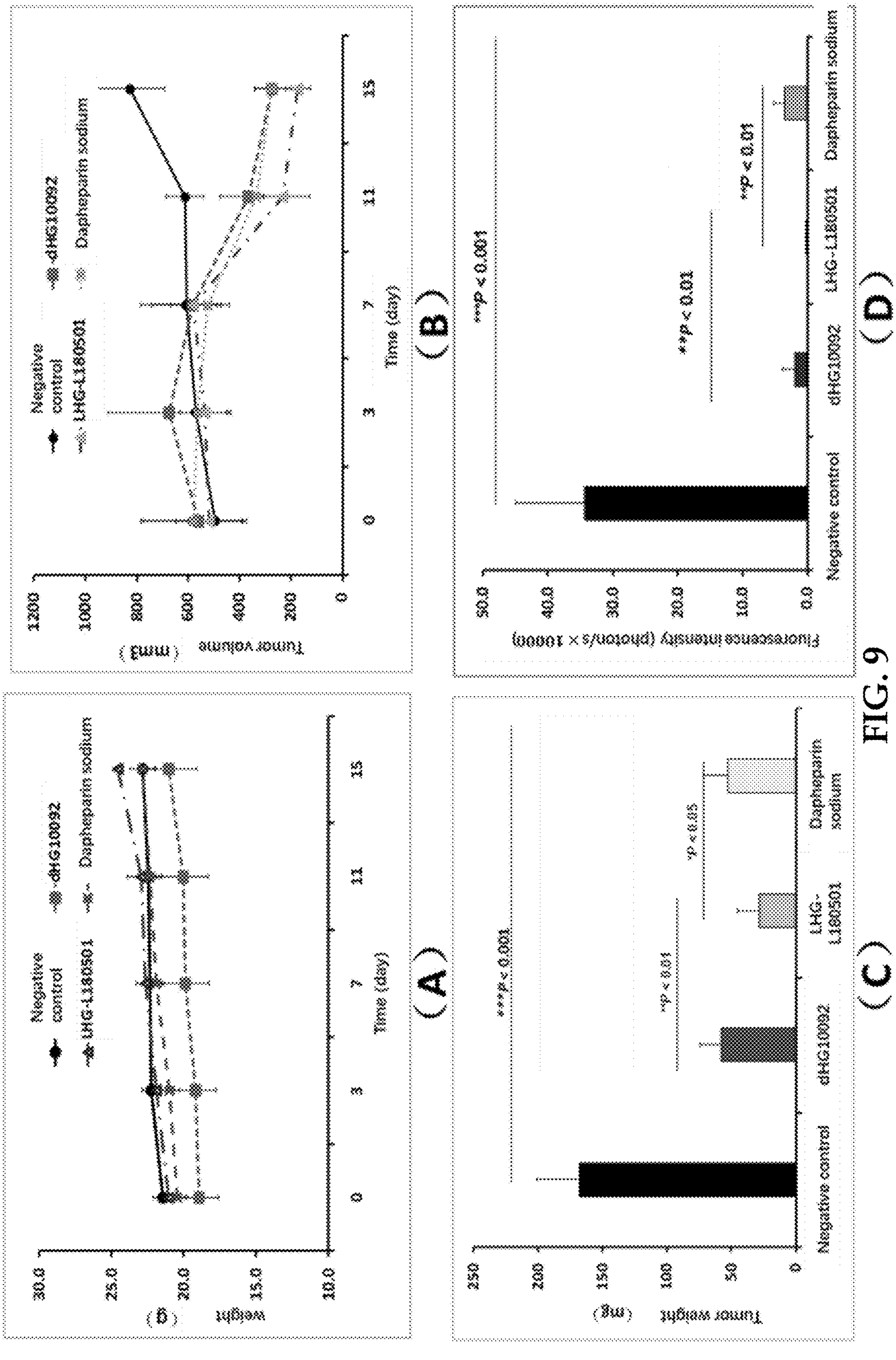
FIG. 9 is the results of influence of LHG on murine SUIT2-LUC (Human Pancreatic Adenocarcinoma Cell) lung metastasis inhibition experiment provided by embodiment 11 of the present invention, wherein the line chart of weight is shown in FIG. 9 (A), the line chart of tumor volume is shown in FIG. 9 (B), histogram of tumor weight is shown in FIG. 9 (C), histogram of fluorescence intensity is shown in FIG. 9 (D), IVIS images of mice and tumor of every group are shown in FIG. 9 (E), IVIS images of lung and tumor of every group are shown in FIG. 9 (F).
Figure 9:
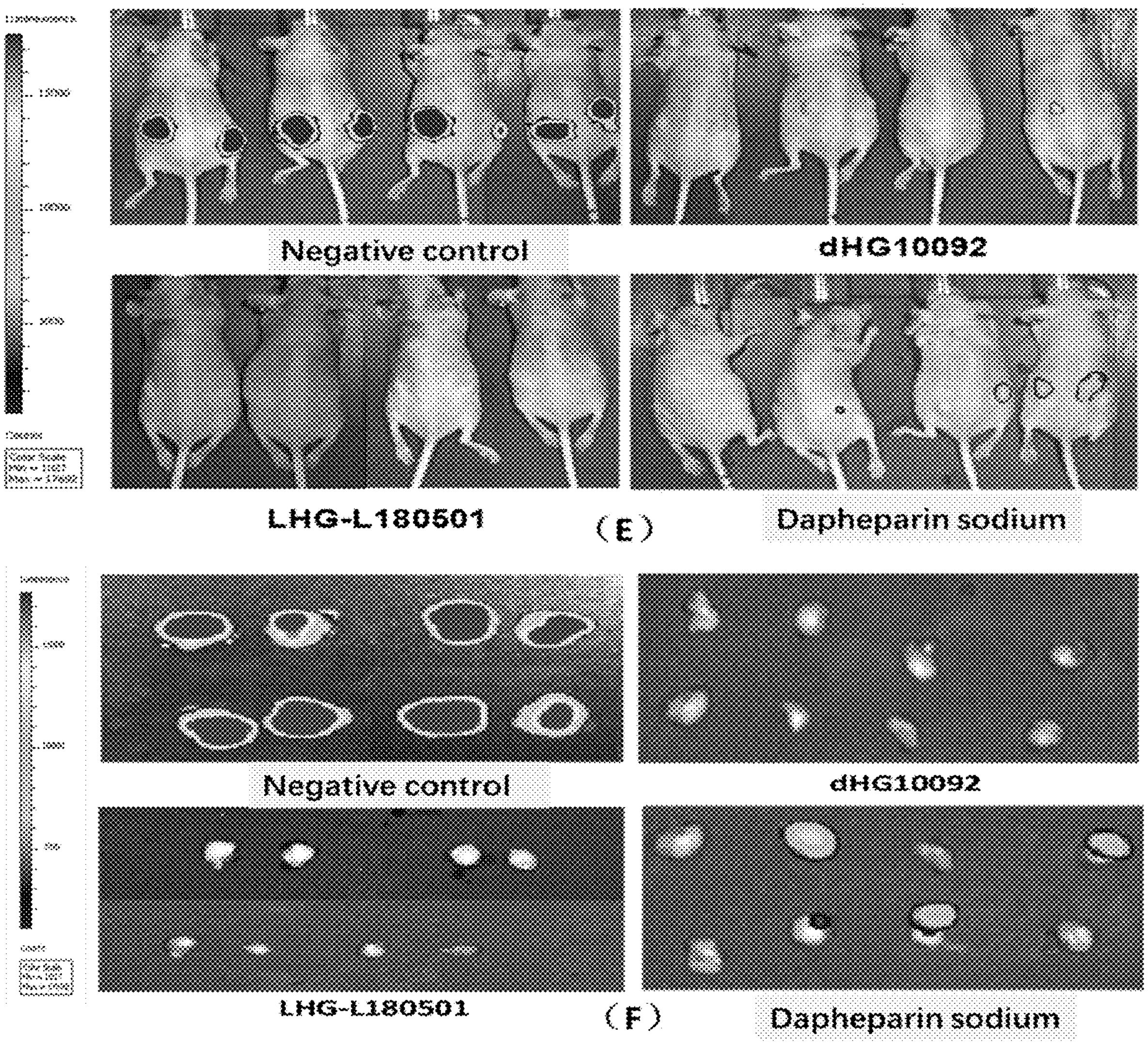

The results of influences of LHG on murine SUIT2-LUC (human pancreatic adenocarcinoma cell) lung metastasis inhibition experiment provided by embodiment 11 of the present invention is shown in FIG. 9. Wherein the line chart of weight is shown in FIG. 9 (A), the line chart of tumor volume is shown in FIG. 9 (B), histogram of tumor weight is shown in FIG. 9 (C), histogram of fluorescence intensity is shown in FIG. 9 (D), IVIS images of mice and tumor of every group are shown in FIG. 9 (E), IVIS images of lung and tumor of every group are shown in FIG. 9 (F). In FIG. 9, every experiment group is: negative control=PBS buffer, dHG10092=dHG control group (30 mg/Kg), LHG-L180501=LHG drug group (30 mg/Kg) and Dapheparin sodium=Dapheparin sodium control group (10 mg/Kg).

As shown in FIG. 9, for the mice of negative control group, due to metastasis and expansion of tumor cells, although weight (A) does not change much, tumor volume (B) increases significantly. For the mice of LHG drug group, dHG control group and Dapheparin sodium control group, weight (A) increases slightly, tumor volume (B), tumor weight (C) and fluorescence intensity (D) decrease significantly. Compared with negative control group, P of LHG drug group, dHG control group and Dapheparin sodium control group is below 0.001. In addition, IVIS images of mice, lung and tumor in vivo of every group are shown in FIG. 9 (E) and FIG. 9 (F), and the fluorescence intensity of tumor cells of LHG drug group, dHG control group and Dapheparin sodium control group decreases significantly compared with that of negative control group, indicating that human pancreatic adenocarcinoma cells SUIT2-LUC are inhibited or killed well. The above experiment results indicate that sulfated polysaccharides (said LHG (LHG-L180501), dHG10092 and Dapheparin sodium) can inhibit significantly the lung metastasis of pancreatic adenocarcinoma cell in mice, and have anti-tumor or anti-tumor metastasis function.

Furthermore, tumor volume (B), tumor weight (C) and fluorescence intensity (D) of LHG drug group decrease significantly compared with those of dHG control group and Dapheparin sodium control group, $P<0.001$ or $P<0.05$. Likewise, IVIS images of mice, lung and tumor in vivo of every group are shown in FIG. 9 (E) and FIG. 9 (F), and the tumor fluorescence signal of LHG drug group mice is almost gone completely compared with dHG control group and Dapheparin sodium control group. The above experiment results indicate that the inhibition of LHG to lung metastasis of pancreatic adenocarcinoma cell in mice is stronger than that of dHG and Dapheparin sodium. Potentially, LHG can be used for prevention and treatment of tumors or tumor metastasis related diseases.

Embodiment 12: Influences of LHG on Rat's Learning and Memory Abilities of Scopolamine Model In this embodiment, LHG's effect of improving rat's learning and memory abilities of scopolamine model was investigated.

Scopolamine is an inhibitor of the central nervous system. Rats injected with scopolamine have weakened learning and memory abilities and spatial cognition ability, and have abnormal enhanced excitability. These behaviors are consistent with the early clinical symptoms of senile dementia patients, so rats injected with scopolamine are often studied as animal models of senile dementia.

1. Materials

Test compound: LHG (batch number is LHG-L180501) prepared in embodiment 1.

Animal: SD rats, 250±50 g, male.

2. Method

Grouping and dose: blank control group, scopolamine model group (SCOP), positive control group:(Donepezil, 1 mg/Kg), LHG drug group (30 mg/Kg).

Administration: intragastric administration. The rats of positive control group and LHG drug group were administered continuously Donepezil or LHG respectively for 2 weeks before test, while the rats of blank control group and scopolamine model group were administered equal volume of distilled water continuously for 2 weeks. Morris training on Day 9 (2 times per day). Morris water maze test and platform jumping test on Day 14.

Modeling method and test of learning and memory: on the day of the test, rats of scopolamine model group, positive control group and LHG drug group were injected with scopolamine hydrobromide through peritoneal cavity (firstly injection dose is 2 mg/Kg for 2 days, then injection dose is 2 mg/Kg on Day 3) at 30 minutes after intragastric administration, while rats of blank control group were injected with equal volume of normal saline through peritoneal cavity. Morris water maze test was conducted at 20 minutes after injection. The route, time and speed of the rats in the 90s were recorded automatically with computer by the camera tracking on the swimming performance of the rats, then the escaping-incubation time of seeking the platform and swimming distance were calculated.

Platform jumping test: Learning and training on the first day, the repeated tests were conducted on the second day. Rats of scopolamine model group, positive control group and LHG drug group were injected with scopolamine hydrobromide through peritoneal cavity (5 mg/Kg) at 20 minutes before the test, while rats of blank control group were injected with equal volume of normal saline through peritoneal cavity. The incubation time of jumping off the platform for the first time (SDL) and the incubation time of avoiding electric shock (EL) were recorded.

3. Results (1) Influences of LHG on Rat's Morris Water Maze Test of Dysmnesia Model Induced by Scopolamine The results of influences of LHG on rat's Morris water maze test of dysmnesia model induced by scopolamine provided by embodiment 12 of the present invention were presented in Table 11.

TABLE 11

| Group | Escaping-incubation time (s) | Swimming distance (cm) |
|---|---|---|
| Blank control group | 20.81 ± 7.93** | 840.14 ± 141.21** |
| SCOP model group | 59.35 ± 16.55 | 2173.42 ± 388.11 |
| Positive control group (Donepezil) | 37.20 ± 12.72* | 1652.25 ± 295.02* |
| LHG drug group | 35.42 ± 9.75* | 1584.05 ± 265.73* |

Compared with scopolamine model group,
*is P < 0.05,
**is P < 0.01.

As shown in Table 11, in the Morris water maze test, LHG improves significantly rat's learning and memory abilities of dysmnesia model induced by scopolamine, the escaping-incubation time and swimming distance decrease significantly. Compared with scopolamine model group, P of LHG drug group is below 0.05. The effect of improving rat's learning and memory abilities of LHG and that of Donepezil are almost equivalent (2) Influences of LHG on Rat's Platform Jumping Test of Dysmnesia Model Induced by Scopolamine The results of influences of LHG on rat's platform jumping test of dysmnesia model induced by scopolamine provided by embodiment 12 of the present invention were presented in Table 12.

TABLE 12

| Group | Incubation time of jumping off the platform for the first time (s) | Incubation time of avoiding electric shock (s) |
|---|---|---|
| Blank control group | 110.53 ± 17.46* | 39.74 ± 10.85* |
| SCOP model group | 23.54 ± 6.92 | 181.65 ± 23.57 |
| Positive control group (Donepezil) | 48.75 ± 9.84* | 115.28 ± 17.54* |
| LHG drug group | 57.62 ± 11.25* | 98.83 ± 16.35* |

Compared with scopolamine model group,
*is P < 0.05.

As shown in Table 12, in the platform jumping test, LHG improves significantly rat's learning and memory abilities of dysmnesia model induced by scopolamine, the incubation time of jumping off the platform for the first time (SDL) increases significantly, while the incubation time of avoiding electric shock (EL) decreases significantly. Compared with scopolamine model group, P of LHG drug group is below 0.01. The effect of improving rat's learning and memory abilities of LHG and that of Donepezil are almost equivalent, even the effect of improving rat's learning and memory abilities of LHG is better than that of Donepezil.

The above experiment results indicate that LHG can improve rat's learning and memory abilities of scopolamine model. Potentially, LHG can be used for prevention and treatment of senile dementia.

Effect of Embodiments

According to the results of embodiment 2-7, It can be seen that LHG disclosed by the present invention retains the structural characteristics of HG derivatives, such as backbone, side chain and saccharide unit, meanwhile contains two unique structural characteristics: one is 10-30% of backbone GlcA are modified, on the 2-position, with a sulfate ester group (the percentage of GlcA2S is 10-30%), another is 10-30% of side chain Fuc is modified, on the 2-position, with an acetyl ester group (the percentage of Fuc2Ac is 10-30%), these two structural characteristics has not been reported.

According to the results of embodiment 2 and embodiment 8, It can be seen that LHG has a low anticoagulant activity, no activity of anticoagulant factor Xa, and has the weak inducing platelet aggregation activity, the applicated security of HLG is high. Therefore, LHG can be used for prevention and treatment of cardiovascular diseases and even tumors potentially.

According to the results of embodiment 9, It can be seen that LHG can decrease significantly the degree of murine auricle swelling induced by xylene, the anti-inflammation effect of LHG and that of dexamethasone are equivalent, and even the anti-inflammation effect of LHG is better than that of dexamethasone. Therefore, LHG can be used for prevention and treatment of inflammation potentially.

According to the results of embodiment 10, It can be seen that LHG can inhibit the activation of AGes-RAGE system, decrease the content of ICAM-1 and VCAM-1 and the content of NO in serum, and alleviate the aortic lesions when LHG acts on vascular lesions in rats of diabetic model induced by streptozotocin. The effect of improving vascular lesions of LHG is better than that of dHG. Therefore, LHG can be used for prevention and treatment of vasculopathy potentially.

According to the results of embodiment 11, It can be seen that LHG can inhibit significantly or kill the metastatic cancer cells when LHG acts on mice of pancreatic adenocarcinoma lung metastasis model, the effect of anti-tumor or anti-tumor-metastasis of LHG is better than that dHG and Dapheparin sodium. Therefore, LHG can be used for prevention and treatment of tumors or tumor metastasis related diseases potentially.

According to the results of embodiment 12, It can be seen that LHG can improve rat's learning and memory abilities when LHG acts on rat of scopolamine model. The effect of improving rat's learning and memory abilities of LHG and that of Donepezil are almost equivalent, even the effect of improving rat's learning and memory abilities of LHG is better than that of Donepezil. Therefore, LHG can be used for prevention and treatment of senile dementia potentially.

According to the results of embodiment 1, in the LHG preparation method of the present invention, firstly, anionic resin adsorption and exchanging elution is directly used to treat the HG released by protease enzymolysis of holothurian homogenate. HG can be separated from conventional impurities with less negative charge, such as protein, fat and nucleic acid, attribute to the feature of strong negative charge carried by the highly sulfate modification in HG. Moreover, purification can be achieved by regulating the concentration of elution salt. This one-step extraction technology with ion exchange resin is extremely simple and efficient, and has not been reported. Secondly, in the depolymerization of subsequent LHG preparation, acetic acid/hydrogen peroxide system is used to catalytic degradation in the present invention, HPLC is used to determinate the molecular weight to monitor the reaction process, low molecular weight LHG with weight-average molecular weight less than 10000 Da can be accurately prepared, and LHG with any weight-average molecular weight can be customized, the LHG preparation method is scientific and reliable. Furthermore, there is no significant difference in the yield between multiple batches of large quantities LHG preparation, the yield is 0.6-0.8%. The raw material of the invention can be holothurian with low edibleness (*Cucumaria japonica*), which is cheap, fruitful and easy to purchase. The holothurian with low edibleness (*Cucumaria japonica*) can also be used in the joint production of other high-value by-products, such as holothurian protein, holothurian polypeptide and holothurian saponins, etc., with great economic value.

In conclusion, LHG disclosed by the present invention has regulating platelet activity, anti-inflammation, anti-vasculopathy, anti-tumor or anti-tumor metastasis functions, and the effect of improving learning and memory abilities. Therefore, LHG can be used as the active substance to prepare drugs or health care products, with acceptable carriers in pharmacy or health care product industry, for the prevention and treatment of inflammation, vasculopathy, tumor, senile dementia and other related diseases.

What is described above is merely the preferred embodiments of the present invention, and it should be noted that numerous improvements and modifications can be made by those skilled in the art without deviating from the principles of the present invention, and these improvements and modifications should also be viewed to be within the scope of the present invention.

What is claimed is:

1. A low-molecular-weight holothurian glycosaminoglycan characterized by the structure shown in the formula below:

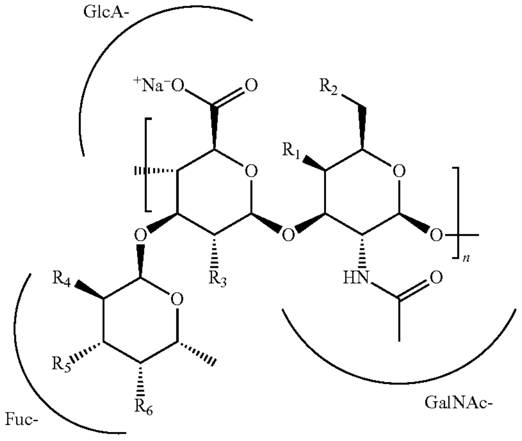

wherein the constituent unit of said low-molecular-weight holothurian glycosaminoglycan includes a glucuronic acid group, an N-acetylaminogalactosyl group, and a fucose group, said glucuronic acid group and said N-acetylaminogalactosyl group are interconnected via β(1-3) and β(1-4) glucosidic bonds to form a backbone of a disaccharide repeating structural unit, and said fucose group is connected to the backbone as a side chain, on a molar ratio basis, the ratio of said glucuronic acid group:said N-acetylaminogalactosyl group:said fucose group is 1:(0.8-1.2):(0.6-1.2), in the structure of said low-molecular-weight holothurian glycosaminoglycan, the n is between 1-32, the $-R_1$, $-R_2$, $-R_4$ and $-R_6$ are hydroxyl groups or sodium sulfate ester, 10%-30% of the $-R_3$ of said glucuronic acid groups is modified with a sodium sulfate ester, and the rest are the hydroxyl groups, 10%-30% of the $-R_5$ of said fucose groups is modified with an acetyl ester group, and the rest are the hydroxyl groups or sodium sulfate ester.

2. A low-molecular-weight holothurian glycosaminoglycan with a sylvite, calcium salt, lithium salt or zinc salt form, wherein said low-molecular-weight holothurian glycosaminoglycan has the structure according to claim 1, but the sodium is replaced with corresponding potassium, calcium, lithium or zinc.

3. A method for treatment of inflammation, comprising administering to a subject in need a medicament or a health-care product comprising the low-molecular-weight holothurian glycosaminoglycan according to claim 1.

4. A method for treatment of vasculopathy, comprising administering to a subject in need a medicament or a health-care product comprising the low-molecular-weight holothurian glycosaminoglycan according to claim 1.

5. A method for treatment of tumors or tumor-related diseases, comprising administering to a subject in need a medicament or a health-care product comprising the low-molecular-weight holothurian glycosaminoglycan according to claim 1.

6. A method for treatment of senile dementia, comprising administering to a subject in need a medicament or a health-care product comprising the low-molecular-weight holothurian glycosaminoglycan according to claim 1.

7. A method for treatment of inflammation, comprising administering to a subject in need a medicament or a health-care product comprising the low-molecular-weight holothurian glycosaminoglycan according to claim 2.

8. A method for treatment of vasculopathy, comprising administering to a subject in need a medicament or a health-care product comprising the low-molecular-weight holothurian glycosaminoglycan according to claim 2.

9. A method for treatment of tumors or tumor-related diseases, comprising administering to a subject in need a medicament or a health-care product comprising the low-molecular-weight holothurian glycosaminoglycan according to claim 2.

10. A method for treatment of senile dementia, comprising administering to a subject in need a medicament or a health-care product comprising the low-molecular-weight holothurian glycosaminoglycan according to claim 2.

11. A medicament or health-care product, comprising the low-molecular-weight holothurian glycosaminoglycan according to claim 1.

12. A medicament or health-care product, comprising the low-molecular-weight holothurian glycosaminoglycan according to claim 2.

* * * * *